(12) United States Patent
Bramley et al.

(10) Patent No.: US 6,875,903 B2
(45) Date of Patent: Apr. 5, 2005

(54) **TREATMENT OF *STAPHYLOCOCCUS* INFECTIONS**

(75) Inventors: A. John Bramley, Hinesburg, VT (US); Karen I. Plaut, Los Gatos, CA (US); David Kerr, Charlotte, VT (US)

(73) Assignee: University of Vermont, Burlington, VT (US)

( * ) Notice: Subject to any disclaimer, the term of this patent is extended or adjusted under 35 U.S.C. 154(b) by 0 days.

(21) Appl. No.: 10/087,667

(22) Filed: Feb. 28, 2002

(65) Prior Publication Data

US 2002/0194629 A1 Dec. 19, 2002

Related U.S. Application Data

(63) Continuation-in-part of application No. 09/337,079, filed on Jun. 21, 1999.
(60) Provisional application No. 60/090,175, filed on Jun. 22, 1998.

(51) Int. Cl.$^7$ ..................... G01N 33/00; A01K 67/00; A01K 67/033; C12N 15/00
(52) U.S. Cl. ................. 800/3; 800/8; 800/21
(58) Field of Search .................. 800/3, 8, 21

(56) References Cited

U.S. PATENT DOCUMENTS

| | | | | |
|---|---|---|---|---|
| 4,931,390 A | 6/1990 | Recsei | ..................... | 435/183 |
| 5,011,772 A | 4/1991 | Recsei | ..................... | 435/69.1 |
| 5,124,145 A | 6/1992 | Sordillo et al. | ............ | 424/85.5 |
| 5,189,015 A | 2/1993 | Hök et al. | ..................... | 514/2 |
| 5,234,684 A | 8/1993 | Sordillo et al. | ............ | 424/85.5 |
| 5,342,612 A | 8/1994 | Daley et al. | ............... | 424/85.1 |
| 5,607,919 A | 3/1997 | Bojsen et al. | ................. | 514/12 |
| 6,028,051 A | 2/2000 | Climo et al. | .................. | 514/2 |

FOREIGN PATENT DOCUMENTS

| | | |
|---|---|---|
| EP | 0 359 873 | 9/1988 |
| EP | 0 759 473 | 8/1995 |
| WO | WO 87/06264 | 10/1987 |
| WO | WO 96/35793 | 11/1996 |
| WO | WO 99/05289 | 2/1999 |

OTHER PUBLICATIONS

Archer, et al., "Human Growth Hormone (hGH) Secretion in Milk of Goats After Direct Tranfer of the hGH Gene into the Mammary Gland by Using Replication–Defective Retrovirus Vectors", *Proc. Nat.Acad. Sci.* 91:6840–44, Jul. 1994.
Auldist, et al., "Changes in the Composition of Milk from Healthy and Mastitic Dairy Cows During the Lactation Cycle", *Aust. J. Exp. Agricul.* 35: 427–36, 1995.
Auldist, et al., "Effect of Somatic Cell Count and Stage of Lactation on the Quality and Storage Life of Ultra High Temperature Milk", *J. Dairy Res.* 63: 377–386, 1996.
Barbano, et al., "Influence of Milk Somatic Cell Count and Milk Age on Cheese Yield", *J. Diary Sci.* 74: 369–88, 1991.
Bramley, et al., "Effects of Lysostaphin on *Staphylococcus Aureus* Infections of the Mouse Mammary Gland", *Research in Veterinary Science*, 49: 120–21; 1990.
Bramley, et al., "Reviews of the Progress of Dairy Science: Mastitis Control—Progress and Prospects" *Journal of Dairy Research*, 51, 481–512, 1984.
Chandler, R.L., "Experimental Bacterial Mastitis in the Mouse", *J. Med. Microbiol.* 3:273–82, 1970.
Craven, et al., "Phagocytosis of *Staphylococcus Aureus* by Bovine Mammary Gland Macrophages and Intracellular Protection from Antibiotic Action in Vitor and In Vivo", *J. Dairy Res.* 51: 513–23, 1984.
Craven, et al., "Antibiotic Activity Against Intraleukocytic *Staphylococcus Aureus* in Vitro and In Experimental Mastitis in Mice", *Am. J. Vet. Res*, 44:(4), 709–12, 1983.
Daley, et al., "Lysostaphin: Immunogenicity of Locally Administered Recombinant Protein Used in Mastitis Therapy", *Veterinary Immunology and Immunopathology*, 31: 301–12, 1992.
Derbyshire, et al., "Immunization Against Experimental Staphylococcal Mastitis in the Goat by the Intramammary Infusion of Cell–Toxoid Vaccine", *Res. Vet. Sci.,*10:559–64, 1969.
Ebert, et al., "Transgenic Production of a Variant of Human Tissue–Type Plasminogen Activator in Goat Milk: Generation of Transgenic Goats and Analysis of Expression", *Bio/Technology*, 9: 835–38, 1991.
Gordon, et al., "Production of Human Tissue Plasminogen Activator in Transgenic Mouse Milk", *Bio/Technology*, 5: 1183–87, 1987.
Harmon, et al., "Concentration of Lactoferrin in Milk of Normal Lactating Cows and Changes Occurring during Mastitis" *Am. J. Vet. Res.*36: 1001–1007, 1975.
Heinrich, et al., "The Molecular Organization of the Lysostaphin Gene and its Sequences Repeated in Tandem", *Mol. Gen Genet*, 209:563–69, 1987.
Jacob, et al., "Potential Therapeutic Applications of Magainins and Other Antimicrobial Agents of Animal Origin", *Ciba. Found. Symp.* 186: 197–216, discussion, 216–23, 1994.

(Continued)

*Primary Examiner*—Joseph Woitach
(74) *Attorney, Agent, or Firm*—Choate, Hall & Stewart

(57) ABSTRACT

The present invention relates to an improved approach for the treatment of microbial infections in mammals. Specifically, the invention provides methods and reagents for expressing in mammalian cells, proteins having antimicrobial activity. The invention provides both genes, which have been modified to allow expression and preferably secretion of active protein in desired mammalian cells or tissues, and methods of introducing such modified genes into desired mammalian cells and/or tissues. Most specifically, genes encoding anti-staphylococcal proteins are delivered to mammalian cells and/or tissues by methods of gene delivery, including gene therapy and the production of transgenic animals, for the treatment of mastitis in ruminant animals.

14 Claims, 20 Drawing Sheets

OTHER PUBLICATIONS

Kagan, et al., "Defensins: A Family of Antimicrobial and Cytotoxic Peptides", *Toxicology,* 87: 131–49, 1994.

Kerr, et al., "Expression of Jet–Injected Plasmid DNA in the Ovine Mammary Gland and In Lymph Nodes Draining the Injection Site", Not much here.

Klei, et al., "Effects of Milk Somatic Cell Count on Cottage Cheese Yield and Quality", *J. Dairy Sci.* 81:1205–13, 1998.

Kossaibati, et al., "Incidence of Clinical Mastitis in Dairy Herds in England", *Vet. Rec.* 143:649–53, 1998.

Krimpenfort, et a., "Generation of Transgenic Dairy Cattle Using 'In Vitro' Embryo Production" *Bio/Technology,* 9: 844–47, 1991.

Liang, et al., "Molecular Cloning and Nucleotide Sequence of the β–Lytic Protease Gene from *Achromobacter Lyticus*" *Journal of Bacteriology,* 172(11):6506–11; 1990.

Maga, et al., "Antimicrobial Properties of Human Lysozyme Transgenic Mouse Milk", *J. Food Prot.* 61: 52–56, 1998.

Maga, et al., "The Effect of Mammary Gland Expression of Human Lysozyme on the Properties of Milk From Transgenic Mice", *J. Dairy Sci.* 78: 2645–52, 1995.

Myllys, et al., "Bovine Mastitis in Finland in 1988 and 1995—Changes in Prevalence and Antimicrobial Resistance", *Acta Vet. Scand.* 39: 119–126, 1998.

Nickerson, et al., "Symposium: Mastitis in Dairy Heifers, Mastitis in Dairy Heifers: Initial Studies on Prevalence and Control", *J Dairy Sci,* 78: 1607–18, 1995.

Nuijens_, et al., "Characterization of Recombinant Human Lactoferrin Secreted in Milk of Transgenic Mice–" *The Journal of Biological Chemistry,* 272 (13): 8802–07, 1997.

Oldham, et al., "Lysostaphin: Use of a Recombinant Bactericidal Enzyme as a Mastitis Therapeutic", *J. Dairy Sci.,* 74: 4175–82, 1991.

Platenburg, et al., "Expression of Human Lactoferrin Milk of Transgenic Mice", *Transgenic Res.* 3: 99–108, 1994.

Plaut, et al., "Integration of the lacZ Gene into the Mammary Gland Using an Adenovirus Vector", *Journal of Dairy Science,* 80:1, 1997.

Recsei, et al., "Cloning, Sequence, and Expression of the Lysostaphin Gene From *Staphylococcus Simulans*", *Proc. Natl. Acad. Sci., USA,* 84: 1127–31, 1987.

Reiter, B., "Review of the Progress of Dairy Science: Antimicrobial Systems in Milk", *J. Dairy Res.* 45: 131–47, 1978.

Sambrook, et al., "Expression of Cloned Genes in Cultured Mammalian Cells", Not much here, Book 3 Chapter 16 pp. 16.1–16.81.

Schindler, et al., Lysostaphin: A New Bateriolytic Agent For the Staphylococcus. *Proc. Natl. Acad. Sci. U.S.A.* 51: 414–421, 1964.

Schnieke, et al., "Human Factor IX Transgenic Sheep Produced by Transfer of Nuclei From Transfected Fetal Fibroblasts", *Science,* 278: 2130–33, 1997.

Shockman, et al., "Structure, Function, and Assembly of Cell Walls of Gram–Positive Bacteria", *Annu. Rev. Microbiol.,* 37: 501–27, 1983.

Sutra, et al., "Virulence Factors Involved in the Pathogenesis of Bovine Intramammary Infections Due to *Staphyolococcus Aureaus*", *J. Med. Microbiol.* 40: 79–89, 1994.

Takahashi, et al., "Nonspecific Antibacterial Factors in Milk from Cows Immunized with Human Oral Bacterial Pathogens", *J. Dairy Sci.* 75: 1810–20, 1992.

Thumm, et al., "Studies on Prolysostaphin Processing and Characterization of the Lysostaphin Immunity Factor (Lif) of *Staphylococcus Simulans* Biovar Staphylolyticus" *Molecular Microbiology,* 23(6), 1251–65, 1997.

Verdi, et al., "Variability in True Protein, Casein, Nonprotein Nitrogen, and Proteolysis in High and Low Somatic Cell Milks", *J. Dairy Sci.* 70: 230–42, 1987.

Wall, et al., "High–Level Synthesis of a Heterlogous Milk Protein in the Mammary Glands of Transgenic Swine", *Proc. Natl. Acad Sci USA,* 88: 1696–1700, 1991.

Watson, et al., "A Field Trial to Test the Efficacy of a Staphylococcal Mastitis Vaccine in Commercial Dairies in Australia".

Williamson, et al., "Expression of Lysostaphin in the Milk of Transgenic Animals to Combat Staphylococcal Mastitis", *J. Appl Bacterial.* 67:6, xxi, 1986.

Williamson, et al., "Expression of the Lysostaphin Gene of *Staphylococcus Simulans* in a Eukaryotic System", *Applied and Environmental Microbiology,* 60:3, 771–76, Mar., 1994.

Wilson, et al., "Bovine Mastitis Pathogens in New York an Pennsylvania: Prevalence and Effects on Somatic Cell Count and Milk Production", *J. Dairy Sci.* 80: 2592–98, 1997.

Wright, et al., "High Level Expression of Active Human Alpha–1–Antitrypsin in the Milk of Transgenic Sheep", *Bio/Technology,* 9:830–34, 1991.

Yamada, et al., "An Autolysin Ring Associated with Cell Separation of *Staphylococcus Aureus*", *J. Bacterial.* 178: 1565–71, 1996.

Yancey, et al., "Activity of Antibodies Against *Staphylococcus Aureus* Within Polymorphonuclear Neutrophils", *Eur. J. Clin. Microbiol. Infect. Dis.* 10:107–113, 1991.

Yarus, et al., "Production of Active Bovine Tracheal Antimicrobial Peptide in Milk of Transgenic Mice", *Proc. Natl. Acad. Sci. USA,* 93, 14118–21, Nov., 1996.

Zavizion, et al., "Effects of *Staphylococcus Aureus* Toxins on the Growth of Bovine Mammary Epithelial Cells (MAC–T) in Culture", *J. Dairy Sci.,* 78, 277–84, 1995.

Figure 11
A.
ORIGIN
```
   1 ccggaactct tgaatgttta gttttgaaaa ttccaaaaaa aaacctactt tcttaatatt
  61 gattcatatt attttaacac aatcagttag aatttcaaaa atcttaaagt caatttttga
 121 gtgtgtttgt atatttcatc aaaatcaatc aatattatt tacttccttc atcgttaaaa
 181 aatgtaatat ttataaaaat atgctattct cataaatgta ataataaatt aggagtatt
 241 aaggttgaag aaaacaaaaa acaattatta tacgagacct ttagctattg gactgagtac
 301 attttgcctta gcatctattg tttatggagg gattcaaaat gaaacacatg cttctgaaaa
 361 aagtaatatg gatgtttcaa aaaaagtagc tgaagtagag acttcaaaag ccccagtaga
 421 aaatacagct gaagtagaga cttcaaaagc tccagtagaa aatacagct aagtagagac
 481 ttcaaaagct ccagtagaaa atacagctga agtagagact tcaaaagctc cagtagaaaa
 541 tacagctgaa gtagagactt caaaagctcc ggtagaaaat acagctgaag tagagacttc
 601 aaaagcccca gtagaaaata cagctgaagt agagacttca aaagccctgg ttcaaaatag
 661 aacagcttta agagctgcaa cacatgaaca ttcagcacaa tggttgaata attacaaaaa
 721 aggatatggt tacggtcctt atccattagg tataaatgc ggtatgcact acggagttga
 781 ttttttatg aatattggaa caccagtaaa agctatttca agcggaaaaa tagttgaagc
 841 tggttggagt aatacggag gaggtaatca aataggtctt attgaaaatg atggagtgca
 901 tagacaatgg tatatgcatc taagtaaata taatgttaaa gtaggagatt atgtcaaagc
 961 tggtcaaata atcggttggt ctggaagcac tggttattct acagcaccac atttacactt
1021 ccaaagaatg gttaattcat tttcaaattc aactgcccaa gatccaatgc ctttcttaaa
1081 gagcgcagga tatggaaaag caggtggtac agtaactcca acgccgaata caggttggaa
1141 aacaaacaaa tatggcacac tatataaatc agagtcagct agcttcacac ctaatacaga
1201 tataataaca agaacgactg gtccatttag aagcatgccg cagtcaggag tcttaaaagc
1261 aggtcaaaca attcattatg atgaagtgat gaaacaagac ggtcatgttt gggtaggtta
1321 tacaggtaac agtggccaac gtatttactt gcctgtaaga acatggaata aatctactaa
1381 tactttaggt gttctttggg gaactataaa gtgagcgcgc ttttataaa cttatatgat
1441 aattagagca aataaaaatt ttttctcatt cctaaagttg aagctt
```

B.
BASE COUNT
ORIGIN
```
   1 gctgcaacac atgaacattc agcacaatgg ttgaataatt acaaaaaagg atatggttac
  61 ggtccttatc cattaggtat aaatggcggt atgcactacg gagttgattt ttttatgaat
 121 attggaacac cagtaaaagc tatttcaagc ggaaaatag ttgaagctgg ttggagtaat
 181 tacgaggag gtaatcaaat aggtcttatt gaaaatgatg gagtgcatag acaatggtat
 241 atgcatctaa gtaaatataa tgttaaagta ggagattatg tcaaagctgg tcaaataatc
 301 ggttggtctg gaagcactgg ttattctaca gcaccacatt tacacttcca aagaatggtt
 361 aattcatttt caaattcaac tgcccaagat ccaatgcctt tcttaaagag cgcaggatat
 421 ggaaaagcag gtggtacagt aactccaacg ccgaatacag gttggaaaac aaacaaatat
 481 ggcacactat ataaatcaga gtcagctagc ttcacaccta atacagatat aataacaaga
 541 acgactggtc catttagaag catgccgcag tcaggagtct aaaagcagg tcaaacaatt
 601 cattatgatg aagtgatgaa acaagacggt catgtttggg taggttatac aggtaacagt
 661 ggccaacgta tttacttgcc tgtaagaaca tggaataaat ctactaatac tttaggtgtt
 721 ctttgggaa ctataaagtg a
```

Figure 12

"MKKTKNNYYTRPLAIGLSTFALASIVYGGIQNETHASEKSNNDV
SKKVAEVETSKAPVENTAEVETSKAPVENTAEVETSKAPVENTAEVETSKAPVENTAE
VETSKAPVENTAEVETSKAPVENTAEVETSKALVQNRTALRNNTHEHSAQWLNNYKKG
YGYGPYPLGINGGMHYGVDFFMNIGTPVKAISSGKIVEAGWSNYGGGNQIGLIENDGV
HRQWYMHLSKYNVKVGDYVKAGQIIGWSGSTGYSTAPHLHFQRMVNSFSNSTAQDPMP
FLKSAGYGKAGGTVTPTPNTGWKTNKYGTLYKSESASFTPNTDIITRTTGPFRSMPQS
GVLKAGQTIHYDEVMKQDGHVWVGYTGNSQRIYLPVRTWNFSTNTLGVLWGTIK"

Figure 13

```
ORIGIN
        1 gccgcaacac atgaacattc agcacaatgg ttgaataatt acaaaaaagg atatggttac
       61 ggcccttatc cattaggtat aaatggcggt atgcactacg gagttgattt ttttatgaat
      121 attggaacac cagtaaaagc tatttcaagc ggaaaaatag ttgaagctgg ttggagtaat
      181 tacggaggag gtaatcaaat aggtcttatt gaaatgatg gagtgcatag acaatggtat
      241 atgcatctaa gtaaatataa tgttaaagta ggagattatg tcaaagctgg tcaaataatc
      301 ggttggtctg gaagcactgg ttattctaca gcaccacatt tacacttcca aagaatggtt
      361 aactcatttt cacagtcaac tgcccaagat ccaatgcctt tcttaaagag cgcaggatat
      421 ggaaaagcag gtggtacagt aactccaacg ccgaatacag gttggaaaac aaacaaatat
      481 ggcacactat ataaatcaga gtcagctagc ttcacaccta atacagatat aataacaaga
      541 acgactggtc catttagaag catgccgcag tcaggagtct taaaagcagg tcaaacaatt
      601 cattatgatg aagtgatgaa acaagacggt catgtttggg taggttatac aggtaacagt
      661 ggccaacgta tttacttgcc tgtgagaaca tggcagaagt ctactaatac tctgggtgtt
      721 ctgtggggaa ctataaagtg a
```

Figure 14

A.
ORIGIN
```
   1 tgtgtgcgtg ctcccattcg ttcatgctcg ccaagcgcac ggccgcgctt tgcgatgcga
  61 tcgcgcaccg tgtgaaccgc attgaggaat ggccgttcgg caagcgcatg tacggcctcg
 121 atttgaacgt gcgtcgcacg acagcgtcgc gcccgcggtc agagtccggc gcccgcggta
 181 tacggacagc gatcgcggcg tcgccgatg acgaacggtc gtgcgcgtca gtcgcatgcg
 241 ccgctcgccg ctggcgttcc ggcttcgcgg gcgcagcgcg gtccaccact cttcaaacgt
 301 cttctcgggg agcagcatat gaagaagatt tccaaggcgg gactggggct ggcgctggtg
 361 tgcgcgctgg cgacgatcgg cggcaacgca gcgcgcaggg ccacggctca gcggcgagga
 421 tctggtgtat tctacgacga gatgttcgac ttcgacatcg atgcgcatct ggccaagcat
 481 gcgccgcatc tgcacaagca ctcggaagag atctcgcact gggcgggcta cagcgggatc
 541 agccgaagtg ttgatcgcgc tgatgagca gcagagcgcg cggtcacgcc aagcgcgcga
 601 cgaatcgtcc gttcggcaag ctggcgcgcg ccgacggctt cggcgcgcag acccgcgagg
 661 tcgcgctggc gctgcgcgag tcgctgtacg agcgcgatcc cgacgcgcca agggcgggt
 721 gacgctggcc cgcgccaatc cgctgcaggc gctgttcgag cgttccggcg acaacgagcc
 781 ggcggccgcg ctgcgcggcg acggcgagtt ccagctggtc tacggcgcc gcgttcaacga
 841 accgcgccag gccaaggcgg cttcggaccg cttcgccaag gccggcccgg acgtgcagcc
 901 gtgtcgccca acggctgct gcagttcccc ttccgcgcg cgccagctg gcatgtcggc
 961 ggcgcccaca ccaacaccgg ctcgggcaat tacccgatgt cgtcgctgga catgtcgcgc
1021 ggcggcgggct ggggcagcaa ccagaacggc aactgggtgt cggcctcggc cgccggctcg
1081 ttcaagcgcc actcttcgtg cttcgcggag atcgtgcaca ccggcggctg gtcgacgacc
1141 tactaccacc tgatgaacat ccagtacaac accggcgcca acgtgtcgat gaacaccgcc
1201 atcgccaacc cggccaacac ccaggcgcag gcgctgtgca acggcgggca gtcgaccggc
1261 ccgcacgagc attggtcgtt gaagcagaac ggcagcttct accacctcaa cggcacctac
1321 ctgtcgggct atcgcatcac cgcgaccggc agcagctatg acaccaactg cagccggttc
1381 tatctgacca agaacggcca gaactactgc tacggctatt acgtcaaccc gggcccgaac
1441 tgaggctcgc cgcgtgcgtt gcccgcgtcc tcaagcgccc cacgcgcggg gcgcgggcac
1501 cggccgggtc aggtcgaatt
```

B.
"MKKISKAGLGLALVCALATIGGNAARRATAQRRGSGVFYDEMFD

FDIDAHLAKHAPHLHKHSEEISHWAGYSGISRSVDRADGAAERAVTPSARRIVRS

ASWRAPTASARRPARSRWRCASRCTSAIPTRQGAGDAGPRQSAAGAVRAFRRQRAG

GRAARRRRVPAGLRPPVQRTAPGQGGFGPLRQGRPGRAAVSPNGLLQFPFPRGASWHVG

GAHTNTGSGNYPMSSLDMSRGGGWGSNQNGNWVSASAAGSFKRHSSCFAEIVHTGG

WSTTYYHLMNIQYNTGANVSMNTAIANPANTQAQALCNGGQSTGPHEHWSLKQNGSFYH

LNGTYLSGYRITATGSSYDTNCSRFYLTKNGQNYCYGYYVNPGPN"

Figure 15

A
ORIGIN
```
   1 gaaaatcca aaaaaaaacc tacttttctta atattgattc atattatttt aacacaatca
  61 gttagaattt caaaaatctt aagtcaatt tttgagtgtg tttgtatatt tcatcaaagc
 121 caatcaatat tatttactt cttcatcgt caaaaatgt aatattcata aaaatatgct
 181 attctcataa atgtaataat aaattaggag gtattaaggt tgaagaaaac aaaaaacaat
 241 tattatacga caccttttagc tattggactg agtacatttg ccttagcatc tattgtttat
 301 ggagggattc aaaatgaaac acatgcttct gaaaaaagta atatggatgt ttcaaaaaaa
 361 gtagctgaag tagagacttc aaaaccccca gtagaaaata cagctgaagt agagacttca
 421 aaagctccag tagaaaatac agctgaagta gagacttcaa aagctccagt agaaaataca
 481 gctgaagtag agacttcaaa agctccagta gaaaatacag ctgaagtaga gacttcaaaa
 541 gctccggtag aaaatacagc tgaagtagag acttcaaaag ctccggtaga aaatacagct
 601 gaagtagaga cttcaaaagc cccagtagaa aatacagctg aagtagagac ttcaaaagct
 661 ccagtagaaa atacagctga agtagagact tcaaaagctc cggtagaaaa tacagctgaa
 721 gtagagactt caaaagcccc agtagaaaat acagctgaag tagagacttc aaaagctcca
 781 gtagaaaata cagctgaagt agagacttca aaagctccgg tagaaaatac agctgaagta
 841 gagacttcaa aagcccagt agaaaataca gctgaagtag agacttcaaa agccctggtt
 901 caaaatagaa cagctttaag agctgcaaca catgaacatt cagcacaatg gttgaataat
 961 tacaaaaaag gatatggtta cggtcctttat ccattaggta taaatggcgg tatccactac
1021 ggagttgatt tttttatgaa tattggaaca ccagtaaaag ctatttcaag cggaaaaata
1081 gttgaagctg gttggagtaa ttacggagga ggtaatcaaa taggtcttat tgaaaatgat
1141 ggagtgcata gacaatggta tatgcatcta agtaaatata atgttaaagt aggagattat
1201 gtcaaagctg gtcaaataat cggttggtct ggaagcactg gttattctac agcaccacat
1261 ttacacttcc aaagaatggt taattcattt tcaaattcaa ctgcccaaga tccaatgcct
1321 ttcttaaaga gcgcaggata tggaaaagca ggtggtacag taactccaac gcccaataca
1381 ggttggaaaa caaacaaata tggcacacta tataaatcag agtcagctag cttcacacct
1441 aatacagata taataacaag aacgactggt ccatttagaa gcatgccgca gtcaggagtc
1501 ttaaaagcag gtcaaacaat tcattatgat gaagtgatga acaagacgg tcatgtttgg
1561 gtaggttata caggtaacag tggccaacgt atttacttgc ctgtaagaac atggaataaa
1621 tctactaata ctttaggtgt tctttgggga actataaagt gagcgcgctt tttataaact
1681 tatatgataa ttagagcaaa taaaattttt ttctcattcc taaagttgaa gcttttcgta
1741 atcatgtcat agcgtttcct gtgtgaaatt gcttagcctc acaattccac acaacatacg
1801 agccggaaca taaagtgcta agcct
```

B
"MKKTKNNYYTTPLAIGLSTFALASIVYGGIQNETHASEKSNMDV

SKKVAEVETSKPPVENTAEVETSKAPVENTAEVETSKAPVENTAEVETSKAPVENTAE

VETSKAPVENTAEVETSKAPVENTAEVETSKAPVENTAEVETSKAPVENTAEVETSKA

PVENTAEVETSKAPVENTAEVETSKAPVENTAEVETSKAPVENTAEVETSKAPVENTA

EVETSKALVQNRTALRAATHEHSAQWLNNYKKGYGYGPYPLGINGGIHYGVDFFMNIG

TPVKAISSGKIVEAGWSNYGGGNQIGLIENDGVHRQWYMHLSKYNVKVGDYVKAGQII

GWSGSTGYSTAPHLHFQRMVNSFSNSTAQDPMPFLKSAGYGKAGGTVTPTPNTGWKTN

KYGTLYKSESASFTPNTDIITRTTGPFRSMPQSGVLKAGQTIHYDEVMKQDGHVWVGY

TGNSGQRIYLPVRTWNKSTNTLGVLWGTIK"

Figure 16 (Page 1 of 2)

ORIGIN
```
   1 gatatcattt caaagacaga tattctaaag aaagatata ttttaaaaaa tgtggttgaa
  61 aaaattaaag aaattcacga ttttgactat atattattg atgtaccacc tattattaac
 121 tctgatttca ctaataatgc tgtttacgca agtgattaca ttttaatggt attccaaaca
 181 caacaatctg cttatgaaag tagtcttica tttgttaatt ttttaaggga tcgaaaaaaa
 241 gaatcagatt tatcatttga attggttggc gctgttccag tattaattaa aaaaagtgga
 301 cgtgtagata aacagatatt agatatgtct aaatcagcat tttctgaagc actctttgag
 361 aaccagatat atcaaagaga aagaataaaa aaatttgccg ctgatggaat aaaagataaa
 421 gatatgcatg acaaaaaagt tatatatatg tttaacaaag tctacgaaga attagttgat
 481 agagttagat taattgaagg tgagtgatat ttatggcagg attttagat aacatagata
 541 catctgaggt aaaatatacg gaaaattata accggtatc taaaagtacg actatgagag
 601 tggacactga tataaaaaaa agattaaatc aaatggcgtt agataaagat acatctataa
 661 aggctatagt tgatgaagtg ttaggagaat tttcgaaaaa aaataagtat tagtatttta
 721 tataggctct ataccattta ggactggtga taatcactag tcctatttt gatacaaaaa
 781 agcgcaatta tctctataat tagaagtatc ctaccaccaa taattaagga aataatgcgc
 841 ctatgtctaa tattatatca atcacccttg gaattaaaga taaaaatatc actttgaag
 901 ataaggttga agaaagtata aagggaaaaa ttcttatt tactttggaa aattaataca
 961 ttctcccaag cgatgtaaac tttgcggaca cgaaaatacg aactttcta taatcaaaaa
1021 tggttttaaa aaatcatgtc ttacgatacc taaggtatcg gagaagccag cttatttaat
1081 attggaaaaa cagcgtttcc actgtaaaaa gtgctgcagt tatttcactg ctgaaacacc
1141 tgtcgttgag tggaattgct atatttctca aaacacacga ttagctgtgc tgaataagtc
1201 gatagacata cgttcgcaaa aatctgttgc tgaatcttgt catgtcagta attccacagt
1261 tactcgaata attaataaag ctgcttctca aatagctcaa acaccgttta aatatttacc
1321 ggaacacttg atgatggatg agttcaaaag cgttaaaaat gttgtcggta aaatgagttt
1381 tatttatgca gatgcagtaa cacaccgtat tattgatatt gtgcctgacc gcaggttatt
1441 tgcttttgaaa aattatttct accgttatcc tctttctgaa agaaaatgtg tgaaagcagt
1501 gtctattgat atgtatgaac cttatatggc tttgatcaga gaagttttc ctaatgccaa
1561 aattctaata gttcatttcc atattgttca gtctttaaat aaagccttga acatgactcg
1621 agtaacagtt atgaatagtt tcagaacaac tgaaagacct ctatacaaca agtacaagcg
1681 ttactggaag attcttttaa aactgccttg aaaaatatag aaatcaatag cgttgctcct
1741 aaacttcaaa cagctgttaa aacactaaga aagcacaata gaatgataag aaatactttt
1801 gaatacagta acttgaccaa cggttcactt gagggaataa atactaaaat aaagctgata
1861 cagagaatat cttctggtta tagaaatttt ggtgatttac gcagtcgtat cattttatgt
1921 acaaatcttt ttgcagctaa tccaaaaaaa gagatcaagc aactttatgc tgcttaatct
1981 ctgcgtttta gctcaccagt cttatttgac agagagccaa taaaattaac ggagggagaa
2041 ggattcgaac caacgcaagc acatacatgc tcctaattaa taaaaatata ttaatcccct
2101 taatccagac ttgggtatcc ctccacaagc attatttaat gctaatataa catatataac
2161 aacaaatgta aatatgtatt tataaggaaa aggatattaa aattattctg agttatataa
2221 ggtagtattc ataatcatcc taaagttgaa gtcgaaaagc ttcaactta ggaatgagaa
2281 aaaatttta tttgctctaa ttatcatata agtttataaa aagcgcgctc actttatagt
2341 tccccaaaga acacctaaag tattagtaga tttattccat gttcttacag gcaagtaaat
2401 acgttggcca ctgttacctg tataacctac ccaaacatga ccgtcttgtt tcatcacttc
2461 atcataatga attgtttgac ctgcttttaa gactcctgac tgcggcatgc ttctaaatgg
2521 accagtcgtt cttgttatta tatctgtatt aggtgtgaag ctagctgact ctgatttata
2581 tagtgtgcca tatttgtttg ttttccaacc tgtattcggc gttggagtta ctgtaccacc
2641 tgcttttcca tatcctgcgc tcttaagaa aggcattgga tcttgggcag ttgaatttga
2701 aatgaatta accattcttt ggaagtgtaa atgtggtgct gtagaataac cagtgcttcc
2761 agaccaaccg attatttgac cagctttgac ataatctcct actttaacat tatatttact
2821 tagatgcata taccattgtc tatgcactcc atcattttca ataagaccta tttgattacc
2881 tcctccgtaa ttactccaac cagcttcaac tattttccg cttgaaatag cttttactgg
2941 tgttccaata ttcataaaaa aatcaactcc gtagtgcata ccgccattta tacctaatgg
3001 ataaggaccg taaccatatc ttttttgta attattcaac cattgtgctg aatgttcatg
3061 tgttgcagct cttaaagctg ttctattttg aaccagggct tttgaagtct ctacttcagc
3121 tgtattttct actgggctt tgaagtctc tacttcagct gtattttcta ccggagcttt
3181 tgaagtctct acttcagctg tattttctac tggagctttt gaagtctcta cttcagctgt
3241 atttttctact ggggcttttg aagtctctac ttcagctgta ttttctaccg gagcttttga
3301 agtctctact tcagctgtat tttctacttc agcttttgaa gtctctactt cagctgtatt
3361 ttctactggg gcttttgaag tctctacttc agctgtattt tctaccggag cttttgaagt
3421 ctctacttca gctgtatttt ctaccggagc ttttgaagtc tctacttcag ctgtattttc
```

Figure 16 (page 2 of 2)

```
3481 taccggagct tttgaagtct ctacttcagc tgtatttct actggagctt ttgaagtctc
3541 tacttcagct gtattttcta ctggagcttt tgaagtctct acttcagctg tattttctac
3601 tggagctttt gaagtctcta cttcagctgt attttctact ggggcttttg aagtctctac
3661 ttcagctact ttttttgaaa catccatatt acttttttca gaagcatgtg tttcattttg
3721 aatccctcca taaacaatag atgctaaggc aaatgtactc agtccaatag ctaaaggtct
3781 cgtataataa ttgttttttg ttttcttcaa ccttaatacc tcctaattta ttattacatt
3841 tatgagaata gcatattttt ataaatatta cattttttaa cgatgaagaa agtaaaataa
3901 tattgattga tttcgatgaa atatacaaac tcactcaaaa attgacttta agattttttga
3961 aattctaact gattgtgtta aaataatatg aatcaatatt aagaaagtag gtttctttctt
4021 ggaatttca aaactaaaca ttcaagagtt cgaagaattc gtgtttcaaa aaatgtctca
4081 ttacacacaa tctgcttctc attttgaata tagaaataac catcagaata atgctgcattt
4141 agttggcgta aaaaatgaaa caggtgaagt attagctgct tgtttactga ctgaggcacg
4201 ttgttttaaag ttctttaaat atttctatac acatcgcggt ccagtcatga actttaaaga
4261 ccatgagtta gtcagatttt tttatgaaaa cttaacgacc tatctaaaaa agcaaaactg
4321 cttatatgtt ttaactgacc cttacctgtt agaaaatatt cgaagttgtg acggagaaat
4381 ccttgaatct tatgataacg aaacttttat gaacgtgatg aatttattag gttaccgtca
4441 tcaagggttt actacaggtt attctcaaac aagtcagatc agatggttgt cggtcttaaa
4501 cctagaaaat aaagatgaaa aacaattgtt aaaagaaatg gattatcaaa cacgccgtaa
4561 tattaagaaa acctatgaaa tgcaggtgaa agtccgcgat ttatcaatta atgaaacaga
4621 tcgattttt aaattattta aaatggctga agaaaaacat ggcttcaaat tcagagaaca
4681 aagttatttt gaaagaatgc agaaaacata cgctgataat agtatgttaa agctggctta
4741 catcgattta gaagaattat tagagacaca aaatgcgaaa gtcgctgagt taaatacaga
4801 tattgaaaat attcaagcgg cattaaaaga aaaccctaat tctaagaaaa acaaaaataa
4861 atatgcgcaa taccaaaagc aattagcagc acaagaacga aaaattactg aaacgaaaaa
4921 attgatagaa acagatggac ctgtattaga cttagctgca gcttactata tctataccc
4981 tcatgaagtt tactacctat ccagtggttc aaaccctaaa tacaatgcct atatgggtgc
5041 gtacagactc caatgggaaa tgattcaatt tgcgaaaaat aaaggtatta atcgctataa
5101 tttttacggt attacaggag atttcagtga agatgctgaa gatttcggtg ttcaaaaatt
5161 caagaaggc tttaatgccc atgttgaaga atatgtcggc gacttcatta aaccgattaa
5221 accttttattt tataaaattc atcaattatt aaatagataa ctgaaaatta tttagtcttt
5281 gttaatcaaa tatgacacct caaatgggt gtgaagagaa ctatattttc aaaggcgtta
5341 atctcgacat cagcgaaggt aaacgttcta gtttttacatt cttaactact aagatgctat
5401 aatttggtta acgaagatta tatgcatatt aagcacctac ttccatcgaa aatatcgccg
5461 gaagataaga cgactatatt attataccat ctgtaaatat acaagcatat atacttctga
5521 taacagaacc ttgtagctga tgctggctat ggtagtaaaa gtaaggtttt gtttcaaagt
5581 aaaaaatata gctaaccact aatttatcat gtcagtgttc actcaacttg ctagcatgat
5641 gctaatttcg tggcatggcg aaaatccgta gatctgaaga gatctgcggt tcttttttata
5701 tagaccgtaa atacattcaa taccttttaa agtattcttt gccgtattga tactttgata
5761 ccttgtcttt cttactttaa tatgacggtg gccttgctca ataaggttat tccgatattt
5821 cgatgtacaa tgacagtcat gttaagtttt aaaagcttta atgactttag ccatggctac
5881 cttcgttgaa ggtgcctgat ctgtaattac cttttgaggt ttaccaaatt gtttaatgag
5941 acgtttgata aacgcatatg ctgaatgatt atctcgttgc ttacgcaagc aaatatctaa
6001 tgtatgggtt ctgtaaaaat taatacttta gaaaacccag cattatatgt atcactgata
6061 ttatatttta tatttcatat aaatacttga acaaaaaatt catatttaat tttctttgtt
6121 gactaacaat atttatttat aagtatttgc tgtcattatt ctaatttatg gaggccgttt
6181 tttatgaact ttaaatattt gtatgagaaa tttcttgga tgagtcttgc ttggattta
6241 gtgtcatgca gtgtcttaag tggtattctg actccctttt gggaattcca ataggtatta
6301 tttttaggctt atatttggat ggattactaa aaaggatgc ttcttgatat taacttaatt
6361 tttaataact ccagctaatt actgttaaag ttgtataatt attaaattaa ggaaacatta
6421 caagaaaagg aaatgcatat ttgtatttcc tttttcttgta atgttataaa aattaagatg
6481 ttatacccta tctttattaa tgctataaac cgtctgcctt gtgatatc
```

Figure 17

"MKKTKNNYYTRPLAIGLSTFALASIVYGGIQNETHASEKSNMDV

SKKVAEVETSKAPVENTAEVETSKAPVENTAEVETSKAPVENTAEVETSKAPVE

NTAEVETSKAPVENTAEVETSKAPVENTAEVETSKAPVENTAEVETSKAPVENTAEVET

SKAPVENTAEVETSKAPVENTAEVETSKAPVENTAEVETSKAPVENTAEVETSKAPVE

NTAEVETSKAPVENTAEVETSKALVQNRTALRAATHEHSAQWLNNYKKGYGYGPYP

LGINGGMHYGVDFFMNIGTPVKAISSGKIVEAGWSNYGGGNQIGLIENDGVHRQWYMH

LSKYNVKVGDYVKAGQIIGWSGSTGYSTAPHLHFQRMVNSFSNSTAQDPMPFLKSAGYG

KAGGTVTPTPNTGWKTNKYGTLYKSESASFTPNTDIITRTTGPFRSMPQSGVLKAGQTIH

YDEVMKQDGHVWVGYTGNSGQRIYLPVRTWNKSTNTLGVLWGTIK"

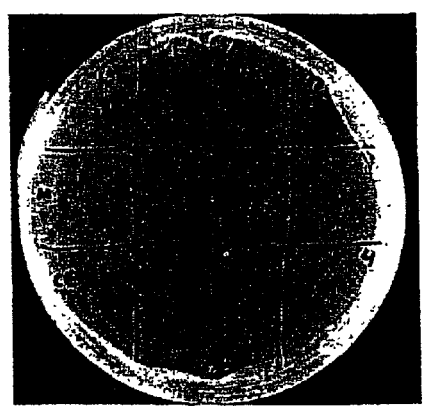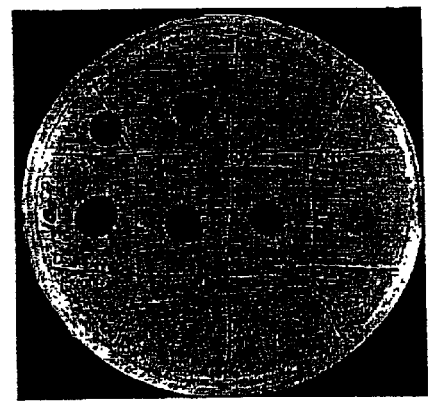
Figure 18

TREATMENT OF *STAPHYLOCOCCUS* INFECTIONS

PRIORITY INFORMATION

This application is a continuation application of U.S. Ser. No. 09/337,079 filed Jun. 21, 1999, now abandoned the contents of which are incorporated herein by reference. The application claims the benefit of priority to provisional application Ser. No. 60/090,175, filed Jun. 22, 1998.

BACKGROUND OF THE INVENTION

Bovine staphylococcal mastitis is a frequent problem for the dairy industry, and leads to estimated annual economic losses of $184 per cow per year. This corresponds to a U.S. total of $1.7 billion per year for milk producers and milk processors. These losses arise from reduced milk yield, reduced compositional quality, lower product quality, and increased veterinary costs.

Mastitis is transmitted from cow to cow at milking time. *Staphylococcus aureus* (*S. aureus*) is a major pathogen that infects both humans and animals which accounts for 15 to 30% of intramammary infection cows. *Staphylococcus* infections are characterized by their persistence and their deleterious effects on milk production and quality. Current therapies and preventative treatments for staphylococcal mastitis rely heavily on sterilization techniques, selective culling of animals with chronic recurring mastitis, and the use of β-lactam antibiotics such as cepharin and penicillin derivatives (Bramley and Dodd, *J. Dairy Res.*, Craven and Anderson, *J. Dairy Res.*, 51:513–523, 1984). Also, numerous attempts have been made to develop vaccines, but none have stood the test of time (Derbyshire and Smith, *Res. Vet. Sci.* 109:559, 1969; Nelson L. et al., *Flem. Vet. J.*, 62 Suppl., 1:111; Rainard et al., *Flem. Vet. J.* 62 Suppl., 1:141; Watson et al., *Proc. Int. Symp. Bovine Mastitis Indianapolis*, 73).

Although sterilization techniques and the use of antibiotics have had a positive impact on dairy animal health and milk production, the prognosis for the elimination of *S. aureus* infection is poor, with often less than a 15% cure rate. This problem may be attributable to incomplete penetration of the antibiotics and/or sequestration of the bacteria within the host cells, leading to relapse of the infection once treatment has ended (Craven and Anderson, supra). The widespread use of antibiotics in dairy animals is also of great concern to the consumer. One problem is accidental exposure of the consumer to the antibiotic drug that can induce a strong immune response resulting in anaphylaxis. There is also a concern that the overuse of antibiotics selects for microorganisms that are resistant to the antibiotic. Many *S. aureus* strains have already acquired resistance to commonly used antibiotics such as ampicillin and penicillin. Such prevalent problems have made it necessary to discard milk for a period of up to 96 hours after antibiotic treatment of an animal, resulting in an enormous waste of milk product and cost to milk producers.

There is a need for the development of an improved approach to treating mastitis infections.

SUMMARY OF THE INVENTION

The present invention provides an improved approach for the treatment of microbial infections in mammals. In particular, the invention provides methods and reagents for expressing in mammalian cells microbial proteins that have anti-microbial, particularly anti-staphylococcal, activity. The invention provides both altered genes, in which the naturally-occurring microbial sequences have been engineered to allow expression of active protein in desired mammalian cells or tissues, and methods of introducing such altered genes into desired mammalian cells and/or tissues. In certain preferred embodiments, an altered gene is modified in such a manner that the protein it encodes is not only produced in mammalian cells but is secreted from those cells, so that a local concentration of anti-staphylococcal protein is created outside of the cells. Most preferably, such cells either are, or are in the vicinity of, cells that are targeted by infectious microbes *S. aureus* for attachment and penetration. In alternative preferred embodiments, an altered gene is prepared so that the anti-microbial protein is expressed within cells that are sensitive to intracellular infection.

The teachings of the present invention are particularly applicable to treatment of staphylococcal mastitis infections in ruminants, such as cows, goats, and sheep; most particularly in cows. In certain preferred embodiments of the invention, the altered gene is delivered to mammary tissue in a form and through a mechanism that allows transient transfection of certain cells, preferably localized within the lining of the teat. In alternative preferred embodiments, the altered gene is delivered through the production of a transgenic animal. Any of a variety of anti-microbial agents may be employed according to the present invention, but one particularly preferred agent is lysostaphin. In preferred embodiments the natural lysostaphin gene is altered to contain one or more of a mammalian promoter, transcriptional regulatory sequence, transcriptional termination signal and/or polyA site, splicing sequences, and translation initiation sequences. Preferred altered genes also include sequences that mediate lysostaphin export from the mammalian cells in which the protein is expressed. Particularly preferred altered genes contain sequence modifications that disrupt one or more post-translational processing events that would otherwise occur upon expression of the lysostaphin protein in the mammalian cells.

DESCRIPTION OF THE DRAWING

FIG. 8 depicts lysis of S. aureus by bioactive lysostaphin produced by 293 cells infected with Ad-hGH-Lys-ΔGLY1-ΔGLY2. Lysostaphin standards were prepared in media. The concentrations were 3 ng/ul, 30 ng/ul and 100 ng/ul. Samples (60 ul) or standards (15 ul) were added to a LB agar plate freshly streaked with S. aureus. Results were evaluated following a 12 hour incubation at 37°. Top row, from left to right: lysostaphin standards at concentrations of 3, 100, 30 ng/ul; middle row, from left to right: cell culture media of 293 cells infected by Ad-hGH-Lys-ΔGLY1-ΔGLY2 isolates #4 and #6, and by 293 cells infected with parent virus Addl 327. Bottom row, from left to right: fresh cell culture media, cell culture media of 293 cells infected by Addl 327, and cell culture media of uninfected 293 cells.

FIG. 11 depicts the entire DNA sequence of the lysostaphin gene cloned by Recsei et al., Proc. Natl. Acad. Sci. U.S.A., 84:1127–1131, 1987 (A), and the DNA sequence encoding the mature lysostaphin protein (Recsei et al., supra) (B).

FIG. 12 depicts the preprolysostaphin amino acid sequence encoded by the lysostaphin gene cloned by Recsei et al., supra.

FIG. 13 depicts the DNA coding sequence of the mature lysostaphin protein of the present invention containing 12 amino acid substitutions, as compared to the Recsei et al. (supra) sequence. The modified sequence encodes a 246 amino acid protein in which all but 2 amino acids are identical to the protein encoded by the Recsei et al. (supra) sequence.

FIG. 14 depicts the DNA sequence of the β-lytic protease gene (Li et al., J. Bacteriol., 172:6506–6511, 1990) (A), and the β-lytic protease amino acid sequence encoded by the β-lytic protease gene (B).

FIG. 15 depicts the lysostaphin DNA sequence cloned by Heinrich et al., (Mol. Gen. Genetic., 209:563–569, 1987) (A), and the amino acid sequence encoded by that gene (B).

FIG. 16 depicts the DNA sequence of the lysostaphin gene cloned by Thumm and Gotz et al., (Molecular Microbiology, 23:1251–1265, 1997). The sequence presented encodes three bacterial genes. Lysostaphin is encoded by nucleotides 725–2018 of the DNA sequence.

FIG. 17 depicts the amino acid sequence of the lysostaphin gene cloned by (Thumm and Gotz et al., supra).

FIG. 18 is a photograph of a bacterial plate assay for staphylolytic activity of milk expressed in mouse mammary tissue. Shown in the top row of the plate, left to right, is bacterially derived lysostaphin 500, 250, 125, and 62 ng/ml. Middle row, left to right: skim milk from the BLG-Lys transgenic mouse high expression line (1.3 mg $Gln^{125,232}$-lysostaphin per ml of milk) diluted 1:200, 1:400, 1:800, or 1:1600. Shown in the bottom row, left to right: skim milk from a non-transgenic mouse diluted 1:200, 1:400, 1:800, or 1:1600.

DESCRIPTION OF THE SEQUENCE LISTING

Figure 1:
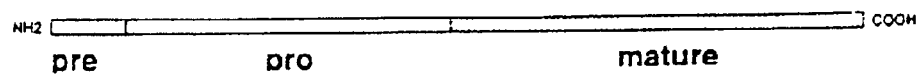
FIG. 1 is a schematic representation of the preprolysostaphin polypeptide.

SEQ ID NO: 1 is the sequence of the naturally-occurring lysostaphin gene of S. simulans (Recsei et al., supra) (FIG. 11).

SEQ ID NO: 2 is the sequence of the naturally-occurring lysostaphin protein. The sequence presented is of the pre-proprotein (FIG. 12).

SEQ ID NO: 3 is the sequence of an inventive altered lysostaphin gene (FIG. 13).

SEQ ID NO: 4 is the β-lytic protease gene from Achromobacter lyticus (FIG. 14).

SEQ ID NO: 5 is a second sequence of a naturally-occurring lysostaphin protein (Heinrich et al., Mol. Gen. Genetic., 209:563–569, 1987) (FIG. 15).

SEQ ID NO: 6 is a third sequence of the naturally-occurring lysostaphin protein (Thumm and Gotz et al., Molecular Microbiology, 23:1251–1265, 1997) (FIGS. 16 and 17).

Definitions

"Altered gene": An "altered" gene, as used herein, is identical to a naturally-occurring gene except that the nucleotide sequence of the altered gene has been modified with respect to that of the naturally-occurring gene through the addition, deletion, substitution, or inversion, of one or more nucleotide residues. Preferred altered genes are those in which the coding sequence of a microbial anti-staphylococcal agent is operatively linked with mammalian expression sequences. Particularly preferred altered genes are those in which at least a portion of the microbial sequence (sufficient to encode a protein with anti-staphylococcal activity) is linked to sequences that direct the secretion of the protein from mammalian cells. Such preferred altered genes may also include sequence modifications that remove (or add) sites for post-transcriptional modifications that would otherwise occur in the mammalian cells. As will be clear to those of ordinary skill in the art, in the context of "altered gene", a "gene" includes expression signals as well as coding sequence.

"Gene": Generally speaking, a "gene", as used herein, is a single transcription unit. However, as will be clear from context and is understood in the art, the term can be used in more than one way. The "gene" for a particular protein always includes the sequence that actually encode the protein. A "gene" may also include regulatory sequences such as sites recognized by transcriptional regulators, or responsible for transcriptional termination. A "gene" may also include intronic sequences and/or splicing signals.

"Microbial host": The term "microbial host" is any self-replicating host of microscopic size that encodes within its nucleic acid genome, an anti-microbial agent. As used herein, "microbial host" can also refer to plants and fungi that encode within their nucleic acid genomes an antimicrobial agent useful in the present invention.

"Naturally-occurring": The term "naturally-occurring" is sometimes used herein to describe microbial genes encoding agents with anti-staphylococcal activity and is intended to refer to the form of the gene (i.e., the gene sequence) that is present in nature, i.e., in the microbial host in which the gene is found. Any self-replicating entity that contains nucleic acid and is found in nature can be a "microbial host" for the purposes of this definition. Moreover, although it is not generally so used in common parlance, the term "microbial host", as used herein, may refer to a plant host.

"Operatively linked": The term "operatively linked" is used herein to refer to nucleic acid sequences that are associated with one another in such a way that they are operative with respect to one another. For example, a promoter is operatively linked to a gene coding sequence when it is associated with that sequence in a manner that allows it to direct transcription of that sequence. Typically, operative linkage involves covalent attachment via a 3'–5' phosphodiester bond. Those of ordinary skill in the art will appreciate that the precise nature of the linkage may vary depending on the nature of the sequences being associated. For example, whereas a promoter is typically required to be 5' (upstream) to gene coding sequences to be operative, other transcriptional regulatory sequences (e.g., enhances) can very often exert effects from upstream, downstream, or within coding sequences, frequently regardless of orientation.

"Recombinant": The term "recombinant", as used herein, refers to a nucleic acid or protein that is produced using the established techniques of recombinant DNA technology (i.e., digestion with restriction endonuclease, ligation, site-specific DNA mutation, polymerase chain reaction, etc.). A recombinant protein is one that is produced from a gene that was made thereof, or from replicative progeny thereof.

"Regulatory sequence": A regulatory sequence is a region of DNA that, when altered or deleted, has an effect on the expression level of the gene with which it is operationally linked. Typically, regulatory sequences are regions of DNA that are recognized (i.e., bound by) protein factors that participate in the regulation of gene expression.

DETAILED DESCRIPTION OF THE PREFERRED EMBODIMENTDS

Altered Anti-Staphylococcal Genes

As mentioned above, the present invention provides altered versions of microbial genes that encode agents with anti-microbial activity, the versions having been modified so that they direct expression of active protein in mammalian tissues or cells.

Those of ordinary skill in the art will appreciate that a significant number of microbial proteins, naturally found in any number of microbial hosts, are known to have anti-microbial activity. In principle, the genes encoding any such proteins could be altered in accordance with the present invention. Preferred genes include those encoding anti-staphylococcal activity, for example, β-lytic protease, lysostaphin, -lytic protease, lyt-M, at1ALE-1, zooA. Other preferred anti-microbial peptides or proteins whose genes could be utilized include lysozyme, nisin, muramidases, glucoasminidases, and colicins. (see, for example Shockman and Barrett, Proc. Natl. Acad. Sci. U.S.A., 51:414–421, 1964; Yamada et al., J. Bacteriol., 178:1565–1571, 1996). Particularly preferred are genes encoding bacteriocins, which are peptide antibiotics that are produced by bacteria and are effective against even closely related species but do not have significant deleterious effects on the species that produces them or on eukaryotic cells. One particularly preferred bacteriocin gene is the lysostaphin gene.

Altered Lysostaphin Genes

Lysostaphin is naturally produced by *Staphylococcus simulans*. Lysostaphin kills closely related staphylococcal species, but does not harm other bacterial species or eukaryotic cells. Lysostaphin has endopeptidase activity and kills cells by hydrolyzing the pentapeptide links of staphylococcal cell walls, causing the cells to lyse (Schindler and Schuhardt, Proc. Natl. Acad. Sci. U.S.A., 51:414–421, 1964). If injected directly into the mammary gland of mice or dairy cattle, recombinant lysostaphin is protective against staphylococcal infection (Bramley and Foster, Res. Vet. Sci., 49:120–121, 1990; Oldham and Daley, J. Dairy. Sci., 74:4175–4182, 1991). The minimum inhibitory concentrations of recombinant lysostaphin against S. aureus are less than 100 ng per ml in culture media and less than 2 μg per ml in milk, (Bramley and Foster, Res. Vet. Sci., 49:120–121, 1990; Oldham and Daley, J. Dairy Sci., 74:4175–4182, 1991). This low concentration requirement makes lysostaphin an attractive candidate for the prevention and treatment of mastitis, because one requirement of the present invention is that the protein be expressed and secreted at sufficient concentrations in vivo to kill S. aureus.

The gene encoding lysostaphin is naturally found on a large plasmid in S. simulans, and encodes a preproenzyme that is processed extracellularly to a mature form, which is active (FIG. 1). Several allelic variations of this gene have been identified that are apparently found in nature (Heinrich et al., supra, (SEQ ID NO: 5) (FIG. 13); Recsei et al., supra, (SEQ ID NO: 1) (FIG. 11); Thumm and Gotz et al., supra, (SEQ ID NO: 6) (FIG. 14); U.S. Pat. No. 4,931,390). The sequence of mature lysostaphin identified by Heinrich, (et al., supra) differs from the sequence identified by Recsei, (et al. supra) by one amino acid, whereas preprolysostaphin has multiple differences. Furthermore, the preprolysostaphin sequence identified by Thumm and Gotz et al., (supra) differs from the preprolysostaphin sequence identified by both Recsei(et al., supra) and Heinrich (et al., supra). According to Thumm and Gotz (et al., supra), preprolysostaphin is 493 amino acids having a signal peptide of 36 amino acids, a propeptide of 211 amino acids and a mature lysostaphin protein of 246 amino acids.

In the present application the term "mature form" refers to a lysostaphin protein which has had the propeptide cleaved off. It should be noted, however, that "active forms" of lysostaphin are not limited to the mature form; other unprocessed forms of lysostaphin also have activity. In particular, preprolysostaphin and prolysostaphin. Prolysostaphin is bioacitve, but mature lysostaphin is 4.5 times more bioactive than prolysostaphin (Thumm and Gotz et al., supra). Variations of lysostaphin that can be modified to be expressed in an active form in mammalian cells fall within the scope of the presently claimed invention.

In order to prepare an altered lysostaphin gene according to the present invention, the naturally-occurring lysostaphin gene sequence must be modified to allow for expression of active lysostaphin protein in mammalian cells. As will be appreciated by those of ordinary skill in the art, expression of bacterial proteins in mammalian cells is often not trivial. Typically, the bacterial coding sequence must be operatively linked to a mammalian, or at least a eukaryotic, promoter and a eukaryotic translation initiation sequence. Although it is often not required that every nucleotide of coding sequence be preserved, or that the coding sequence initiate and terminate at precisely the same points as it does in its natural host system (fusion proteins and modest deletions are usually tolerated), it is essential that the coding sequence to be employed be operatively linked to expression signals that are effective in the cells into which the altered gene is to be introduced.

A large number of different eukaryotic, and particularly mammalian, expression signals are known in the art and include promoters, transcriptional regulatory sequences (often provided in conjunction with the promoter with which they are naturally associated or with a promoter with which they have previously been experimentally associated), transcriptional termination signals, splicing signals, translation initiation signals, post-transnational processing signals, and secretory signals (see, for example, *Current Protocols* 16.0–16.21.9). Those of ordinary skill in the art will appreciate that not every one of such signals must be employed in an altered gene of the present invention. It is generally preferred to include eukaryotic (preferably mammalian) transcription and translation initiation signals; other sequences may be employed as necessary or desirable. Various other modifications may also be made.

Promoters that may be employed include constitutive promoters, inducible promoters, universal promoters (i.e., active in substantially all cell types), and/or tissue specific promoters. Those of ordinary skill in the art will appreciate that the precise application of the inventive altered gene will determine which category of promoter is more desirable. For example, if expression is desirably limited to a particular tissue, a tissue-specific promoter is employed; if expression is desirably limited to times when certain environmental conditions are present, an inducible promoter responsive to those environmental conditions is employed. Particular promoters are also selected on the basis of their ability to direct higher or lower levels of transcription.

As mentioned above and discussed more fully below, in certain preferred embodiments of the present invention, an altered lysostaphin gene is to be expressed in mammary tissue. If the altered gene is to be introduced only into mammary cells, a tissue-specific promoter is not required. Preferred promoters for use in such circumstances include, but are not limited to, Cytamegalo virus, (CMV), Rous Sarcona Virus (RSV) and human elongation factor 1 (EF-1) α subunit. Particularly preferred is the CMV promoter. Of course, a tissue-specific promoter may nonetheless be employed. Known mammary-specific promoters include, for example, β-lactoglobulin, α-lactalbumen, caseins and whey acidic protein. Particularly preferred is the β-lactoglobulin promoter.

The Kozak sequence is well established to be the eukaryotic translation initiation sequence and is the preferred sequence to be introduced into altered genes of the present invention.

Williamson and colleagues have previously reported that operative linkage of the entire lysostaphin gene to the human cytomegalovirus promoter and the Kozak initiation sequence is sufficient to direct expression of lysostaphin in COS-7 cells, but active enzyme was not secreted from the cells (Williamson et al., *Appl. Environ. Microbiol.*, 60:771–776, 1994). The low level of activity detected by William et al. (supra) (less than 1 ng/ml) is likely due either to release from lysed cells and a small amount of protein that escapes glycosylation in the in vitro system.

Figure 2:
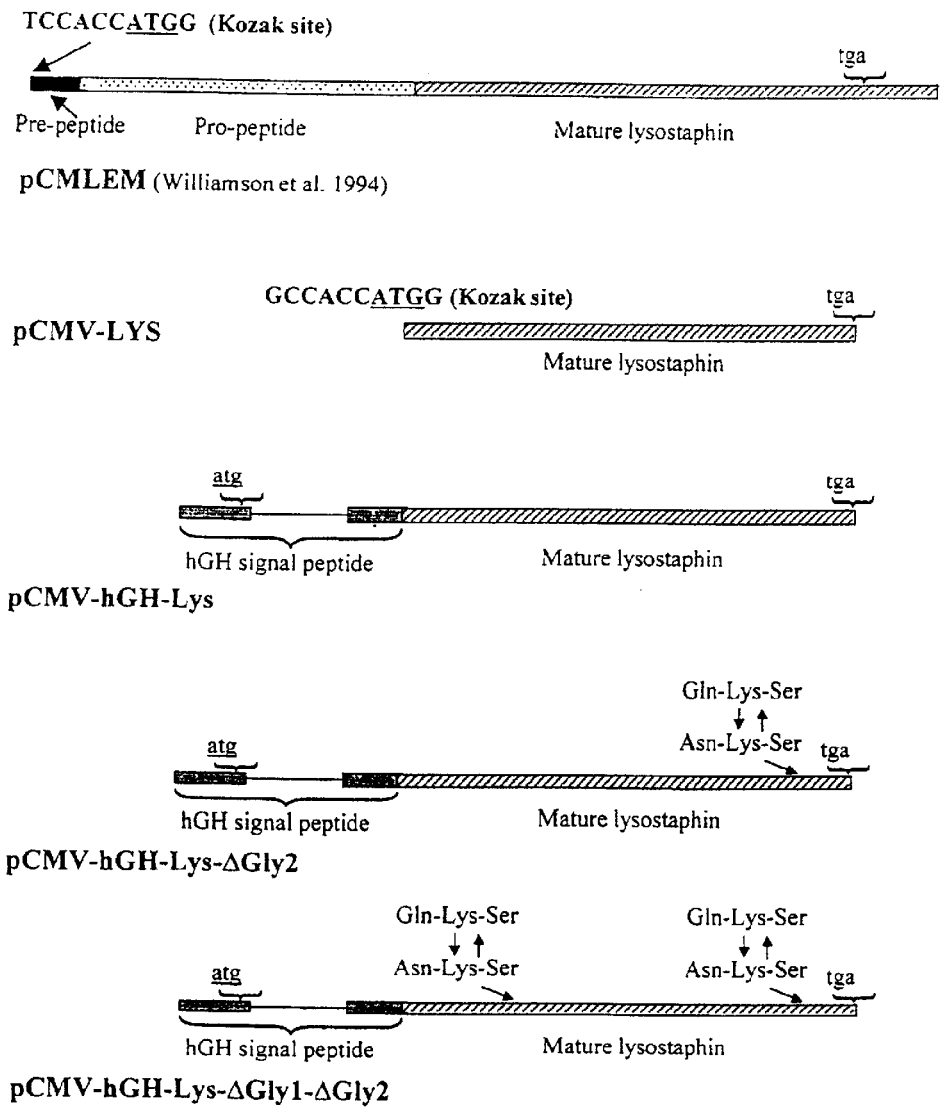
FIG. 2 is a representation of modifications of the lysostaphin gene for eukaryotic expression.
Figure 3:
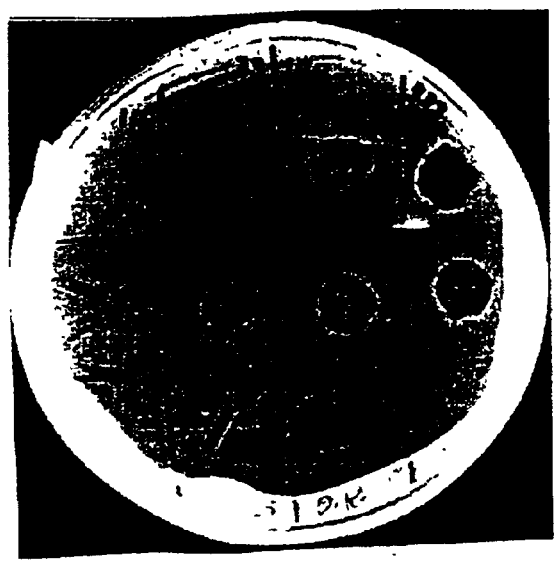
FIG. 3 is an experiment demonstrating lysis of *S. aureus* by bioacitve lysostaphin produced by COS-7 cells transfected with pCMV-Lys. Top row, lysostaphin standards at concentrations of 10, 33, 100, and 333 ug/ml; middle row, blank, 1×, 2×, 4× cell extract; bottom row, blank, 1×, 2×, 4× conditioned media.

As described in Example 1 and FIG. 2, we have prepared an altered version of the lysostaphin gene that directs production and secretion of active lysostaphin from mammalian cells. Our first attempt at producing an active, secreted lysostaphin in mammalian cells utilized a construct, pCMV-Lys, in which the coding sequence for mature lysostaphin was operatively linked to the cytomegalovirus promoter and the bovine growth hormone polyadenylation signal. This construct, like that described by Williamson et al., (supra) was sufficient to produce lysostaphin in mammalian cells, but did not produce active secreted protein (FIG. 3).

In an effort to correct this problem, we produced a second construct, pCMV-hGH-Lys, that included a mammalian signal peptide to direct secretion of the lysostaphin protein from the cell. Those of ordinary skill in the art will appreciate that any of a number of different signal peptides could have been used including, but not limited to, β-lactoglobulin, caseins, erytropoietin, and insulin, so long as they were linked in-frame to the lysostaphin coding sequence. We elected to use the human growth hormone signal peptide, because expression and secretion of the entire human growth hormone gene had previously been demonstrated in the ruminant mammary gland (Kerr et al., *Anim. Biotechnol.* 7:33–45, 1996). Moreover, the human growth hormone signal peptide had previously been used to direct the secretion of engineered proteins from Chinese hamster ovary cells (Peccu et al., *Gene,* 97:253–258, 1991).

Figure 4:
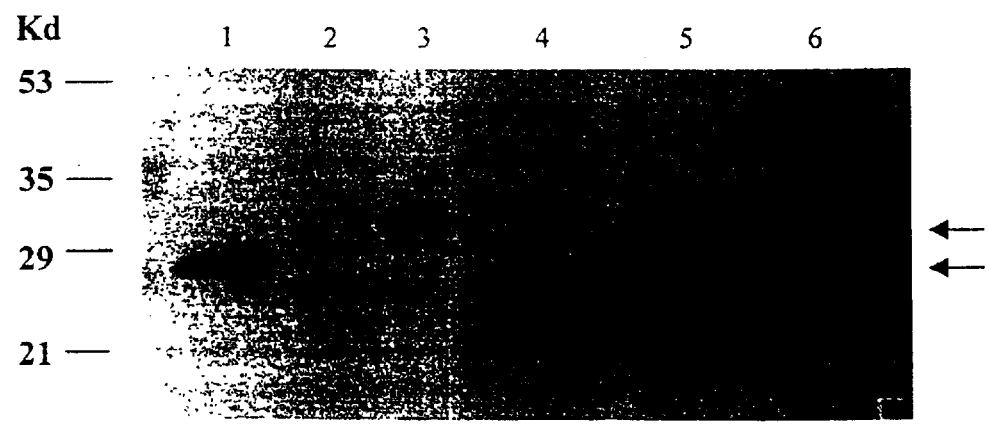
FIG. 4 is a Western blot of conditioned media samples treated with or without N-glycosidase-F. Molecular size standards are shown on the left. Samples in lanes 1, 2, and 3 were untreated, and contain 20 ul of media from COS-7 cells transfected with: pCMV-hGH control, spiked with 1 ug/ml lysostaphin (lane 1), pCMV-hGH control (lane 2), pCMV-hGH-Lys (lane 3). Samples in lanes 4 and 6 were incubated with deglycosylation buffers, no enzyme, for 16 hours, 37°. Sample in lane 5 was incubated with deglycosylation buffers, and enzyme, for 16 hours, 37°. Lanes contain 20 ul of media from COS-7 cells transfected with pCMV-hGH (lanes 4), pCMV-hGH-Lys (lanes 5, 6).

In analyzing the inactive lysostaphin produced from our second construct, we noted that it had a molecular weight of approximately 33 Kd, somewhat larger than the lysostaphin standard that migrated at 28 Kd (FIG. 4). We hypothesized that post-translational processing events, in particular glycosylation events, might be disrupting the activity of the lysostaphin produced in mammalian cells. Other post-translational processing events that might affect biological activity include methylation, disulfide bond formation, acetylation, phosphorylation and sialylation. As those of ordinary skill in the art will appreciate, bacterial proteins are not normally glycosylated. However, when such proteins are expressed in a mammalian system, there is the possibility that the mammalian cell will recognize putative glycosylation steps within the sequence of the bacterial protein, and will add glycosyl groups that may alter the activity of the protein. Glycosylation of lysostaphin during secretion inactivates the lysostaphin protein. Consequently, it may be desirable to modify the potential glycosylation sites to prevent deactivation of the lysostaphin protein by glycosylation during secretion.

We scanned the lysostaphin protein sequence for possible glycosylation sites that might be recognized in a mammalian expression system. We identified two instances of the sequence Asn-X-(Ser/Thr), which can be recognized by mammalian N-linked glycosylation machinery. We confirmed that exposure of the protein to N-glycosidase F, which removes N-linked glycosyl groups, reduced the apparent molecular weight of the protein to that of the lysostaphin standard (FIG. 4).

In light of these findings, we prepared new constructs in which we had modified one or both of the N-linked glycosylation sites by substituting Gln for Asn (FIG. 2). Those of ordinary skill in the art will recognize that any of a variety of other approaches could be used to disrupt a potential N-linked glycosylation site, but substitution is generally preferred over addition or deletion of residues. Conservative substitutions (i.e., substitutions with amino acids of comparable chemical characteristics) are particularly preferred. For the purposes of conservative substitution, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid.

We found that removal of both glycosylation sites resulted in production of an active, secreted lysostaphin from mammalian cells (see Examples 1 and 5). We note that this observation of active lysostaphin secreted from mammalian cells is the first such demonstration. In fact, prior work evidences the difficulty of achieving active secreted protein. In particular, WO 96/35793, reports detection of very large amounts (100 to 250 ng/ml/24 hours) of lysostaphin protein in cell extracts, but little or no activity of that material. Accordingly, an "altered lysostaphin gene" of the present invention is a lysostaphin gene whose sequence has been modified as compared with that of naturally-occurring lysostaphin (SEQ ID NO:3) in that lysostaphin coding sequence sufficient to encode at least mature lysostaphin has been (i) operatively linked to mammalian expression signals sufficient to direct expression of the gene product in mammalian cells; (ii) operatively linked to a mammalian signal peptide such that the expressed gene product is secreted from the mammalian cells in which it is produced, and, preferably, (iii) modified such that at least one, and preferably both, of the Asn-X-(Ser/Thr) N-linked glycosylation sites is disrupted. Alternatively, it may be desirable to eliminate the signal peptide to permit intracellular accumulation of the anti-microbial protein.

As mentioned above, the lysostaphin coding sequence that is useful in the production of altered lysostaphin genes according to the present invention is not limited to the mature lysostaphin sequence; the preprolysostaphin and prolysostaphin sequences have also been shown to produce active proteins, although expression of the immature form of lysostaphin is substantially less than that of the mature form. Moreover, as will be appreciated by those of ordinary skill in the art, various changes to the precise lysostaphin amino acid sequence can readily be made without interfering with (and sometimes promoting, as seen in the glycosylation site examples) lysostaphin activity. So long as the lysostaphin amino acid sequence does not differ so extensively from that presented as SEQ ID NO:2 that activity is lost, the sequence may be used in accordance with the present invention. Those of ordinary skill in the art are well familiar with techniques for modifying amino acid sequences (see, for example, Sambrook, J. et al., *Molecular Cloning: A Laboratory Manual*, Cold Spring Harbor Press, N.Y., incorporated herein by reference), and may employ any known technique, including those described herein, to assay the proteins produced from genes containing such modifications in order to determine whether such genes encode functional proteins as required by the present invention. Altered genes that direct expression and secretion of an active lysostaphin protein with one or more sequence differences from naturally-occurring lysostaphin (SEQ ID NO:1) or from the particular altered lysostaphin described herein (SEQ ID NO:3) are considered to be "functional equivalents" of the altered lysostaphin described herein, and are within the scope of the present invention.

Additional modifications to the lysostaphin gene that fall within the scope of the present invention include, for example, nucleotide substitutions that more accurately reflect eukaryotic codon usage without altering the amino acid sequence of the encoded protein (see, for example, (Sambrook et al., supra). Such changes are expected to enhance the efficiency of translation and the amount of protein being produced. Another modification involves removal or disruption of a potential polyadenylation signal near the 3' end of the lysostaphin gene.

Altered β-Lytic Protease Genes

Another preferred bacterial gene for use in the production of altered genes according to the present invention is the β-lytic protease gene (SEQ ID NO:4) from *Achromobacter lyticus* (Li et al., *J. Bacteriol.*, 172:6506–6511, 1990). β-lytic protease exhibits potent bacteriolytic activity on *Micrococcus lysodeikticus* and *S. aureus*. It is approximately 25-fold more potent than lysostaphin on heat killed *S. aureus*, and approximately 40-fold more potent than lysostaphin on viable *S. aureus* (Li et al., *J. Biochem.* (Tokyo), 122: 772–778, 1997).

An altered β-lytic protease gene according to the present invention is produced, as was the case with the lysostaphin gene, by operatively linking β-lytic protease coding sequence with (i) a mammalian promoter; (ii) a mammalian translation initiation sequence; and (iii) a mammalian signal peptide. Additional modifications may also be made.

Other Altered Genes

Any of a variety of other genes encoding agents with anti-microbial activity may also be employed in accordance with the present invention. As discussed above, a variety of different microbial anti-staphylococcal agents are known. Any gene encoding such an agent may be modified as described herein to produce an altered gene of the present invention. Useful genes may be isolated from any natural source, including bacteria, fungi, plants, and other microbes.

These other anti-staphylococcal genes are modified to produce altered genes of the present invention through operative linkage with (i) a mammalian promoter; (ii) a mammalian translation initiation sequence; and (iii) a mammalian signal peptide. Additional modifications may also be made. For example, some such genes may have introns, or sequences that are recognized as introns, that are inappropriately spliced in a mammalian system. Such inappropriate splicing events can be identified, for example, by isolating mRNA from a mammalian cell transfected with a version of the gene that has been modified to include the mammalian promoter, translation initiation sequence, and signal peptide. Inappropriate splicing may be corrected by alteration of inappropriate splice sites, or removal of intronic sequences. However, it is often desirable to maintain (or introduce) at least one intron in an altered gene, as intron-containing genes are often more efficiently expressed in mammalian systems (see, for example, Wall and Seidel, *Theriogenology*, 38:337–357).

Also, the mammalian signal peptide might not be properly cleaved from the protein produced upon expression of a modified gene containing a mammalian promoter, translation initiation sequence, and signal peptide in a mammalian cell. Inappropriate signal peptide cleavage may be identified by immunopurification of the expressed protein, which is then analyzed by polyacrylamide gel electrophoresis and/or N-terminal sequencing. Problems with signal peptide cleavage can generally be corrected through selection of a different signal peptide, such as one from one of the major milk proteins.

Additionally, as discussed above, modifications may be made to introduce mammalian codons without changing protein sequence, to remove or disrupt any putative glycosylation sites and/or polyadenylation signals, etc.

Finally, those of ordinary skill in the art will recognize that the principles taught by the present invention are readily applicable to genes encoding proteins or peptides with anti-microbial (including anti-viral) activity other than, or in addition to, anti-staphylococcal activity. For example, as mentioned above, *Staphylococcus aureus* accounts for up to only 30% of intra-mammary infections (Nickerson et al., *J. Dairy Sci.*, 78:1607–1618, 1995). It will be clear to one skilled in the art that the other 70% of intra-mammary infections are due to other pathogens and therefore any protein with anti-bacterial activity that would combat the offensive pathogen could be delivered to the mammary gland for treatment of mastitis. Furthermore, multiple genes could be delivered to the mammary gland simultaneously (see further discussion below).

Introduction of Altered Genes into Mammalian Expression Systems:

The altered anti-microbial genes of the present invention may be introduced into mammalian cells or tissues in order to treat or prevent infection of those tissues. In vitro transfection methods that introduce DNA into mammalian cells in culture are well known in the art and include calcium phosphate transfection, DEAE-dextran transfection, electroporation, and liposome-mediated transfection.

In the present invention, it is preferred that the method of protein expression utilize methods that transfer DNA into living cells in vivo. In certain embodiments, the genes are delivered by somatic cell engineering, or gene therapy. In such circumstances, the genes are not delivered to the animal's offspring, and are often (unless retroviral delivery systems are employed) only transiently expressed in the cells to which they are delivered.

A variety of systems are available for delivering altered genes to somatic cells, either systemically or locally, in accordance with the present invention (see, for example, Ausubel et al., *Current Protocols in Molecular Biology*, Greene Publishing Associates, New York, V. 1&2, 1996 and Kerr et al., *Anim. Biotechnol.*, 7:33–45, 1996). Such systems include, but are not limited to, high-pressure jet injection, lipisome-based delivery systems, and viral delivery systems, including both retroviral and standard viral systems.

The mammalian cells and tissues into which the altered genes of the present invention are to be produced include any mammalian cells or tissues. Preferred cells and tissues are within ruminants such as cows, sheep, and goats, but also include humans. Also, although mammary tissue is one particularly preferred tissue for expression (see below), any tissue that is susceptible to or that has microbial infection, is a desirable expression site according to the present invention.

Notwithstanding the foregoing, expression in mammary tissue is a particularly preferred aspect of the present invention. Thus, in preferred embodiments of the invention, the delivery system is selected, in combination with the gene modifications, to ensure that the altered gene is expressed in mammary tissue. In one particularly preferred embodiment, an altered anti-staphylococcal gene is delivered locally to mammary epithelial cells via the teat canal. This route of intramammary infusion administration has the greatest chance of transfecting the epithelial cells lining the teat or teat duct, which are a prime target for attachment and invasion by staphylococcal species and therefore are also an important target for the production of anti-microbial proteins. Alternatively, in another preferred embodiment, delivery of plasmid DNA into lactating sheep mammary parenchyma can be achieved by high-pressure jet-injection. This method achieves transfection of cells within the narrow path of the injectate (Kerr et al., *Anim. Biotechnol.*, 7:33–45, 1996).

Altered anti staphylococcal genes can be delivered to the epithelial cells of the mammary gland by non-viral approaches (Hyde et al., *Nature*, 362:250–255, 1993; Oudrhiri et al., *Proc. Natl. Acad. Sci. U.S.A.*, 94:1651–1656, 1997; Hens et al., *Molecular Biology of the Cell, Suppl*, 1996). Non-viral approaches generally rely on liposome carriers to enhance transfection efficiency. For example, transfection of guinea pig mammary gland with the human growth hormone gene resulted in accumulation of up to 500 ng/ml of the human growth hormone in milk (Hens et al., supra).

In other preferred embodiments of the present invention, viral vector approaches are utilized to achieve transient transfection of mammary epithelial cells with inventive altered genes. Viral vector approaches include retro-(Kay et al., *Science*, 262:117–119, 1993), adeno-(Smith et al., *Nat. Genet.*, 5:397–402, 1993), and adeno-associated viruses (Floret, *J. Bioener. Biomembr.*, 25:37–42,1993). Retrovirus infection results in integration of the viral nucleic acid sequence into the host cell DNA, causing permanent transfection of that cell. Retroviruses can only infect dividing cells, but have been shown to be capable of transfecting the caprine mammary gland during a period of hormone-induced mammogenesis (Archer et al., *Proc. Natl. Acad. Sci. U.S.A.*, 91:6804–6844, 1994).

Figure 7:
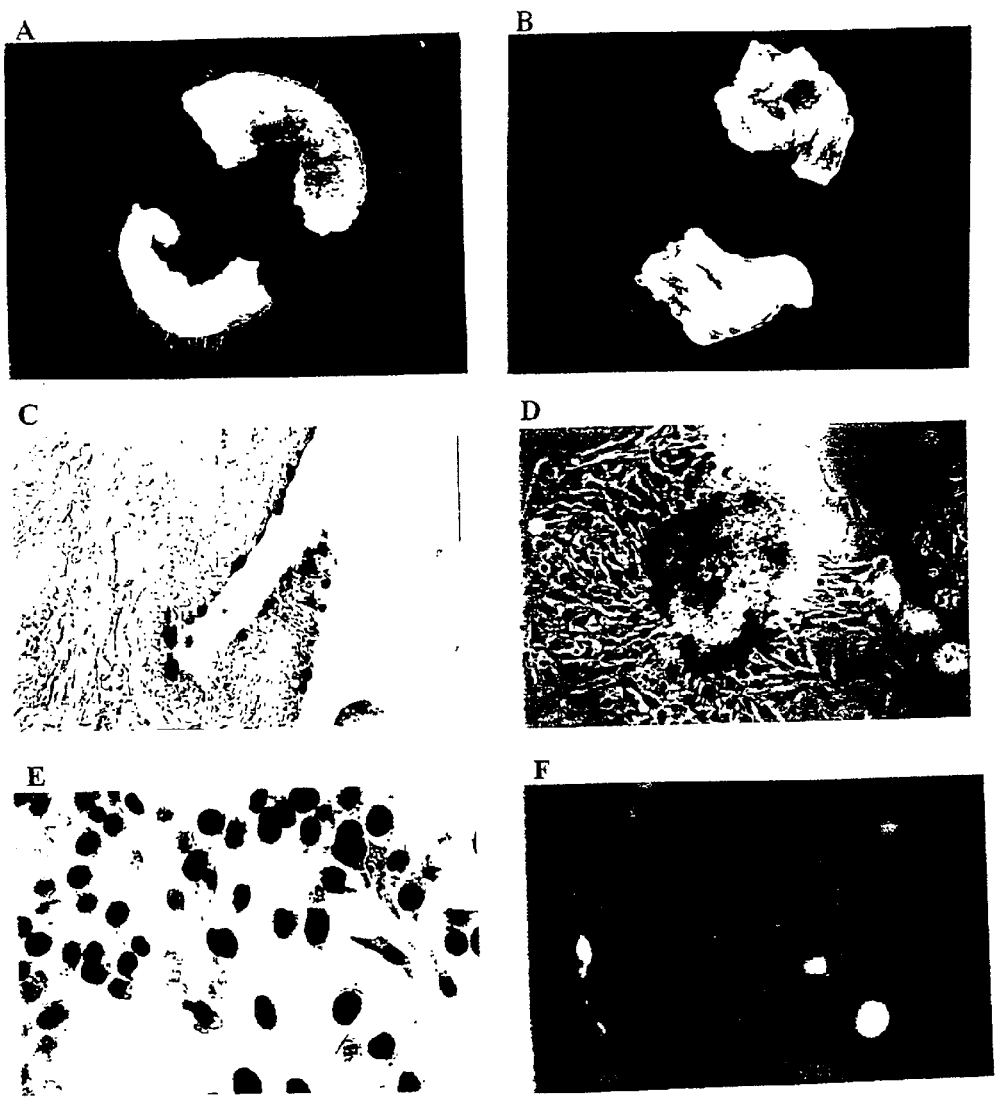
FIG. 7 shows tissue fragments, tissue section and cultured cells, exposed to the X-gal reagent for visualization of β-galatosidase activity (panel A–E). (A) Teat tissue, (B) adjacent mammary tissue, (C) sections of teat tissue (40×), (D) primary culture of mammary tissue from one goat mammary gland transfected with LacZ-containing adenovirus (Av1Lac4) by intramammary infusion. The contralateral gland was infused with vehicle and blue staining was not observed (lower tissue pieces panel A and B). (E) Bovine mammary epithelial cell line (BME-UV) following transfection with AvLacZ4. (F) Green fluorescent protein in COS-7 cells transfected with the GFP gene.
Figure 3:
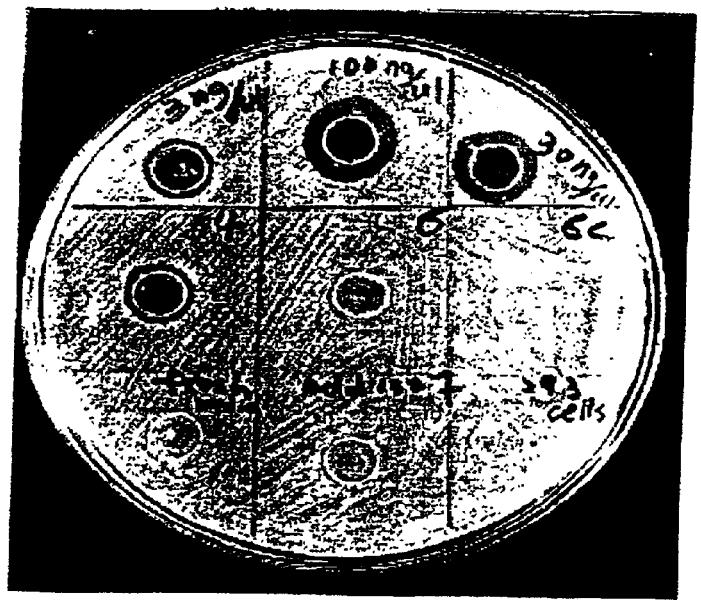

In a particular preferred embodiment, an adenovirus vector is used to deliver altered anti-staphylococcal genes to bovine mammary epithelial cells. The adenoviral-based method of gene delivery has several advantages over retroviral-based gene delivery in that transfection efficiency is higher and it can infect non-dividing cells. New adenoviral vectors have also been developed that limit the host antiviral immune response, which is common to adenoviral transfection. A strong cellular immune response can greatly reduce the persistency of andenoviral-mediated gene expression and precludes repeated administration of the same vector (Ilan et al., *Proc. Natl. Acad. Sci. U.S.A.*, 94:2587–2592, 1997; Chen et al., *Proc. Natl. Acad. Sci. U.S.A*, 94:1645–1650, 1997; Smith et al., (supra). We have demonstrated that an adenoviral vector systems can be successfully employed for delivery of genes to the ruminant mammary (Plaut et al., *J. Dairy Sci.*, 80, Suppl. 1, 155 (Abstract), 1997) (see Example 2). Direct administration of adenovirus containing the β-galactosidase gene to the teat of a goat resulted in intense blue staining of the entire lining of the teat canal (see FIG. 7). Mammary tissues were also infected. This finding is readily generalizable to the inventive altered genes, which may therefore also be delivered to ruminant mammary cells through adenoviral transfection (see Example 3).

Those of ordinary skill in the art will appreciate that it will sometimes be desirable to express more than one inventive altered gene simultaneously in the same mammalian cells or tissue. With this multi-gene approach, not only is the spectrum of the bactericidal activity improved, but the likelihood of bacterial resistance development is substantially diminished.

Transgenic Animals

The altered genes of the present invention may also be introduced into mammalian cells through transfer into mammalian germ line cells and subsequent production of transgenic animals. Established methods for such germ line transfer include, but are not limited to, micro injection of DNA into one-cell embryos (Gordon et al., *Proc. Natl. Acad. Sci U.S.A.*, 77:7380–7384, 1980), transfer of genetically engineered embryonic stem-cells into blastocysts (Hooper et al., *Nature*, 326:292–295, 1987; Kuehn et al., *Nature*, 326:295–298, 1987), and the transfer of nuclei from engineered cells into enucleated oocytes (Campbell et al., *Nature*, 380:64–66, 1996). Germ genetically engineered cells to oocytes (Schnieke et al., *Science*, 278:2130–2133, 1997) result in a permanent change in the animal's genome and the genomes of its offspring.

Germ cell engineering has become wholly routine in the area of transgenic mice (Gordon et al., *Biotechnology*, 5:1183–1187, 1987), and has also been broadly applied to pigs (Wall et al., *Proc. Natl. Acad. Sci. U.S.A.*, 88:1696–1700, 1991), sheep (Wright et al., *Biotechnology*, 9:830–834, 1991), goats (Ebert et al., *Biotechnology*, 9: 835–838, 1991), and cattle (Krimpenfort et al., *Biotechnology*, 9:844–847, 1991). To give but one relevant example, Gordon et al., (*Biotechnology*, supra) have created transgenic mice that produced human tissue plasminogen activator in transgenic mouse milk. Any of the techniques described in these references, or otherwise known in the art, may be employed to create transgenic animals in which an altered gene of the present invention has been stably introduced into their genome. Such transgenic animals are useful not only as staphylococcus-resistant creatures, but as bioreactors for the production of anti-staphylococcal agents for use in the treatment of others.

Peptide Antibiotics

Peptide antibiotics are widespread in nature, being found in plants, animals, and prokaryotes. Animal antibacterial proteins include lysozyme, lactoferrin, and a class of antimicrobial compounds known as defensins. Lysozyme is a muramidase to which Gram negative and some Gram positive microorganisms, such as *S. aureus*, show varying degrees of resistance (for reviews, see Reiter et al., "Protective Proteins in Milk-Biological Significance and Exploitation", *International Dairy Federation Bulletin* #191. IDF, Square Vergote 41, 1040—Brussels, Belgium; Maga and Murray, *J. Dairy Sci.*, 78:2645–2652, 1995). It is normally present in human milk at approximately 100 μg per ml and in ruminant milk at less than 1 μg per ml, yet the role lysozyme may play in the prevention of mastitis is presently unknown. However, lactoferrin, which acts as an antimicrobial through its iron-chelating activity (Reiter et al., supra), does protect the non-lactating mammary gland from infection by *E. coli*, although this inhibition is lost at the time of calving (Bramley, *J. Dairy Res.*, 43:205–211, 1976). This is exemplified by the fact that the concentration of lactoferrin in normal milk, which is about 200–300 μg/ml, is unable to prevent infection, and the concentration of lactoferrin in milk in infected cows, which is in excess of 1 mg/ml, is unable to cure infection.

Furthermore, the defensins, produced in neutrophils, macrophages, and epithelial cells lining mucosal surfaces (Kagan et al., *Toxicology*, 87:131–149, 1994), also have antibacterial action resulting from their ability to form pores in susceptible cellular membranes. One particular defensin, bovine tracheal antimicrobial peptide (TAP) has antibacterial activity in vitro against *E. coli* and *S. aureus*, with minimum inhibitory concentrations (Diamond et al., *Proc. Natl. Acad. Sci. U.S.A.*, 88:3952–3956, 1991; Yarus et al., *Proc. Natl. Acad. Sci. U.S.A.* 93:14118–14121, 1996) and would therefore be a likely candidate for use in the present invention. Analogous peptides to the defensins, called magainins, have been isolated from amphibian skin and are being evaluated as topical antibiotics for human medicine (Jacob and Zasloff, *Ciba Found. Symp.* 186:197–216 discussion 216–223, 1994). So far, the activity of these cationic peptides in milk is compromised, presumably through binding to phosphorylated caseins or inserting into the milk fat globule membrane.

EXAMPLES

The present invention can be further understood through consideration of the following non-limiting Examples.

Example 1

Genetic Engineering of the Lysostaphin Gene

A. Construction of New Lysostaphin Expression Plasmids

In an attempt to increase production and secretion of lysostaphin, four new expression constructs were prepared (FIG. 2). All four constructs were made by inserting modified lysostaphin genes into the polylinker of the 5.4 Kb eukaryotic expression vector, pcDNA3 (Invitrogen). The vector contains the CMV promoter and the bovine GH polyadenylation signal, with an intervening polylinker.

All four lysostaphin constructs were generated by a PCR-based technique in which the 5' primer included a 5' Not I restriction site and the 3' primer included a 3' Apa I site. The primers were positioned such that only the coding region and the TGA stop codon of the mature portion of the lysostaphin gene were amplified. We used pCMLEM (Simmonds et al., *Appl. Environ. Microbiol.*, 62:4536–4541, 1996) as the lysostaphin template, and the resulting Not I-Lysostaphin-Apa I amplicons were cloned between the Not I and Apa I sites in the pcDNA3 polylinker. The nucleotide sequences of all PCR-generated fragments were confirmed with an automated cycle-sequencing technique at the University of Vermont molecular diagnostics laboratory.

The expression plasmid pCMV-Lys was constructed by inserting a short linker sequence 5' to the mature lysostaphin sequence, between the Bam HI and Not I sites of the pcDNA3 polylinker. The short sequence was prepared from two custom 13 base oligonucleotide (Gibco/BRL), and resulted in the addition of a Kozak sequence and a start codon (ATG) to the lysostaphin gene. These features, which are required for efficient translation initiation, encode the insertion of an additional N-terminal amino acid (methionine) to the lysostaphin protein. This engineered protein does not contain a signal peptide and thus would not be transferred to the golgi apparatus for glysosylation and secretion.

The expression plasmid pCMV-hGH-Lys was constructed by inserting the human growth hormone (hGH) intron-containing signal peptide coding region, 5' to the mature lysostaphin sequence. This eukaryotic signal peptide was chosen to enhance the secretion of lysostaphin from the cells. We have previously had satisfactory experience with the expression of the entire hGH gene in the ruminant mammary gland (Kerr et al., *Anim. Biotechnl.,* 7:33–45, 1996), and it has been used by others to direct the secretion of engineered proteins (Pecceu et al., *Gene,* 97:253–258, 1991). The coding region of the hGH signal peptide included the 5' untranslated region and the first intron of the hGH gene. The intronic sequence was included, as there is good evidence that introns increase expression of foreign proteins (Wall and Seidel, Jr., *Theriogenology,* 38, 337–357, 1992). The modified hGH signal peptide was obtained from a collaborator (Dr. K. Wells, GEML-ARS-USDA, Beltsville, Md.). The resulting hGH-lysostaphin sequence codes for the amino acids of the entire hGH signal peptide immediately followed by the entire mature form of lysostaphin. The sequence of this construct was confirmed by DNA sequencing.

The expression plasmids pCMV-hGH-Lys-ΔGly2 and pCMV-hGH-Lys-ΔGly1-ΔGly2 were subsequently prepared. A PCR strategy was used to remove glycosylation sites from the mature lysostaphin gene and generate pCMV-hGH-Lys-ΔGly2 and pCMV-hGH-Lys-ΔGly1-ΔGly2. pCMV-hGH-Lys-ΔGly2 removes one of two potential N-linked glycosylation sites within mature lysostaphin. The final construct, pCMV-hGH-Lys-ΔGly1-ΔGly2, was designed to encode a lysostaphin protein in which both N-linked glycosylation sites (Asn-X-Ser/Thr) have been removed by mutation of the site's Asn codons to Gln codons (FIG. 2). Bacterial proteins are not normally glycosylated, but when expressed in a eukaryotic system, any Asn-Xxx-Ser/Thr sequence of amino acids in a protein has the potential for N-linked glycosylation. The plasmids pCMV-hGH-Lys-ΔGly2 and pCMV-hGH-Lys-ΔGly1-ΔGly2, were constructed in a similar fashion to pCMV-hGH-Lys. However, the 3' primer for generating the lysostaphin amplicon contained nucleic acid substitutions that resulted in a change from AAT to CAG at the codon for amino acid number 232 of the mature lysostaphin protein. This causes an asparagine to glutamine change in the encoded protein, and thus destruction of the potential glycosylation site. We chose to convert Asn to Gln based on the similar structure and characteristics of their side groups. The plasmid pCMV-hGH-Lys-ΔGly1-ΔGly2 was similarly constructed using a synthetic 5' primer. The Asn to Gln strategy was recently reported as being successful in preventing the glycosylation of a bacterial enzyme that was engineered to be expressed on the cell surface of eukaryotic cells (Marais et al., *Nat. Biotechol.* 15:1373–1377, 1997). Importantly, these authors reported considerable enzymatic activity of the modified protein was maintained, even with three Asn to Gln mutations.

B. Evaluation of Lysostaphin Expression Plasmid In Vitro

Lysostaphin expression from the four new constructs was evaluated following their transfection into COS-7 cells. The cells were transfected in six-well culture plates, with a $CaPO_4$ precipitation technique (Sambrook et al., *Molecular Cloning: A Laboratory Manual,* Cold Spring Harbor Press, N.Y., 1989, incorporated herein by reference). Following exposure to the plasmid precipitate, cells were washed and then incubated with 1 ml DMEM containing 10% FBS for 48 hours Media was then collected, cleared by centrifugation, and stored (−20°). Cell extracts were obtained by freeze/thaw disruption of the cell monolayer with 0.5 ml phosphate buffered saline (PBS). Transfection efficiency was monitored visually by co-transfection with a green fluorescent protein (GFP) expression plasmid. The plasmid, pCMV-GFP, was constructed by inserting the GFP encoding fragment from pEGFP-NI (Clontech) into pcDNA3. Plasmid DNA used in transfections contained a 9:1 mixture of the test plasmid and pCMV-GFP. Consistently high (>50%) transfection efficiencies were obtained (FIG. 7F).

Figure 5:
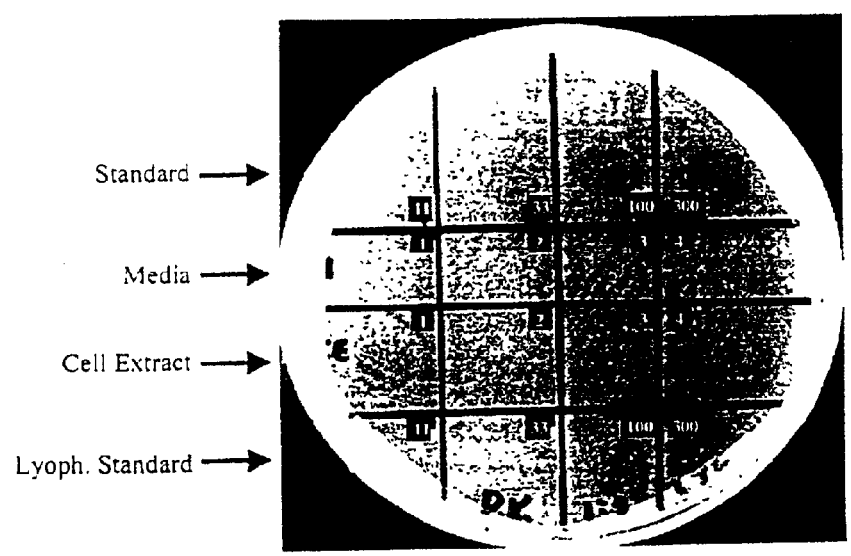
FIG. 5 is a bacterial plate assay for detection of lysis of *S. aureus* (M60) by media or cell extracts from transfected COS-7 cells. Media and cell extracts were obtained 48 hours post transfection with (1) pCMV-Lys, (2) pCMV-hGH-Lys, (3) pCMV-hGH-Lys-ΔGly1-ΔGly2, (4) pCMV-hGH genomic as a control. Conditioned media or cell extracts were lyophilized and resuspended with one third the original volume of H₂O. Top row: lysostaphin standards at concentrations of 11, 33, 100 or 300 ng/ml in media. Second row: conditioned media, Third row: cell extracts. Bottom row: lysostaphin standards that were diluted 1:3 in media, lyophilized, and resuspended with one third the original volume of H₂O.

Cell extracts from COS-7 cells transfected with the signal peptide devoid construct, pCMV-Lys, exhibited bacteriolytic activity using plate assay technique (FIGS. 3s and 5). Specifically, conditioned media or cell extracts were lyophilized and resuspended with the original volume (1×), 0.5 volume (2×), or 0.25 volume (4×) of $H_2O$. Lysostaphin standards were prepared in media. Samples or standards (15 ul) were then applied to an LB agar plate freshly streaked with *S. aureus* and incubated 16 hours, 37°. For the plate assay, aliquots of the cell extract or conditioned media were spotted onto culture plates that had been freshly streaked with *S. aureus* (strain M60). Following an overnight incubation, clear lytic zones were observed. We estimated the lysostaphin concentration to be ≈50 ng/ml by comparison with standard preparations containing a commercial lysostaphin preparation (Sigma L-7386). No activity was detected in media, presumably because the lysostaphin gene lacked a signal peptide. No activity was detected in media or cell extracts from cells transfected with control plasmid, pCMV-hGH. Thus, the COS-7 cells are capable of producing lysostaphin, and the lysostaphin appears to be non-toxic.

Figure 6:
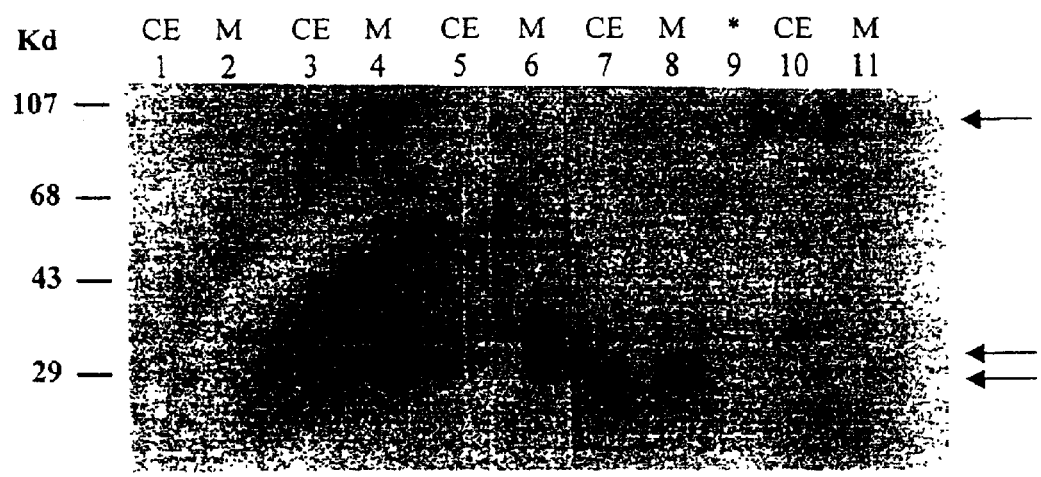
FIG. 6 represents Western blot analysis of lysostaphin expressed in transfected COS-7 cells. Molecular size standards are shown on the left. Lanes contain 50 µl cell extract (CE), or media (M), respectively, from cells transfected with: pCMB-hGH as control (lanes 1, 2), pCMV-hGH-Lys (lanes 3, 4), pCMV-hGH-Lys-ΔGly2 (lanes 5, 6), pCMV-hGH with standard lysostaphin protein added to 1 µg/ml (lanes 7, 8), Ad-preprolysostaphin (lanes 10, 11). Lane 9 (*) contained culture media and Ad-preprolysostaphin as used for infection.

Lysostaphin bioactivity was not detected using the *S. aureus* plate assay, in either media or cell extracts from COS-7 cells transfected with pCMV-hGH-Lys. However, substantial lysostaphin immunoreactivity was observed by Western blot assay of media, but not extracts, of cells transfected with pCMV-hGH-Lys (FIG. 6, lane 4). Proteins were separated on a 12% polyacrylamide-SDS gel, transferred to nitrocellulose membranes and probed with a rabbit anti-lysostaphin polyclonal antibody. Bound antibodies were detected with an alkaline phosphatase-linked second antibody and BCIP/NBT substrate. The band representing lysostaphin migrated with an apparent molecular weight of ≈33 Kd, somewhat larger than the lysostaphin standard that migrated at ≈28 Kd. Media samples were estimated to contain ≈200 ng/ml of immunoreactive lysostaphin. To determine if the larger molecular weight of the engineered protein was due to N-linked glycosylation, samples were deglycosylated by overnight incubation with N-glycosidase-F (Boehringer-Mannheim). A clear reduction in the apparent molecular weight of the expressed protein, compared to that of the lysostaphin standard, was observed (FIG. 4, lane 5). Thus, addition of the hGH signal peptide region to pCMV-Lys directed the secretion of relatively large quantities of a glycosylated inactivated lysostaphin protein by COS-7 cells. The 26 amino acid signal peptide, which has a predicted molecular weight of 2.7 Kd, was apparently cleaved, as the deglycosylated protein had a similar molecular weight to the lysostaphin standard.

Transfection with the pCMV-hGH-Lys-ΔGly2 construct did not result in the desired increase in activity or size reduction of COS-7 produced lysostaphin. The media, but not cell extracts, obtained from these transfections contained similar levels of similar sized immunoreactive lysostaphin as those resulting from pCMV-hGH-Lys transfections (FIG. 6, lane 6).

Transfection of the Eucaryotic cell line, COS-7, with the pCMV-hGH-Lys-ΔGly1-ΔGly2 construct, that encodes a lysostaphin protein in which both N-linked glycosylation sites have been removed reveals bioactive lysostaphin in the culture media but not in the cell extracts (see FIG. 5). Strong, yet indirect evidence for secretion of the protein, rather than cell lysis and release into media, is found by comparison of results obtained from the signal peptide devoid construct pCMV-Lys to the new construct containing the hGH signal peptide, pCMV-hGH-Lys. Without the signal peptide, lysostaphin accumulates within the cells such that cell extract, but not media, cause bacterial cell lysis. This media likely does contain some lysostaphin resulting from cell lysis, but the concentration is below the detection limits of our assay. However, with the hGH signal peptide and the deglycosylation construct, bioactive lysostaphin is detected only in the media, not in the cell extract. Presumably the cell extract contains an amount of bioactive lysostaphin that is below detection. No bioactivity is observed from cells transfected with the construct containing the hGH signal peptide and the unmodified lysostaphin gene.

Example 2

Adenovirus Mediated Expression of β-Galactosidase

A. Propagation of Av1LacZ4

The plasmid Av1LacZ4 (Genetic Therapy Inc; Bethesda, Md.) is a replication deficient, recombinant, human type 5 adenovirus that contains the gene for nuclear targeted β-galactosidase (LacZ) (Smith et al., supra). The E3 region of this adenovirus has been deleted and the β-galactosidase gene replaces the E1a region rendering the virus replication incompetent. Viral stocks were prepared using the 293 packaging cell line (ATCC #CRL-1573). This cell line is a stable transfectant that produces the Ad 5 E1a transcription factor and thus complements the E1a deletion in the recombinant virus. Briefly, confluent 293 cells were infected with the virus and 36 hours later the propagated virus particles recovered by 5 cycles of freeze/thawing. A cleared lysate was obtained by low speed centrifugation, and a purified preparation was obtained following two rounds of CsCl density-gradient ultracentrifugation. The CsCl was removed by extensive dialysis against sterile 10 mM Tris pH 7.4, 1 mM $MgCl_2$, 10% glycerol. Viral stocks were stored at −70°. Titres of the viral stocks were determined by plaque assay using 293 cells.

B. Infection of a Ruminant Cell Line With Av1LacZ4

To confirm integrity of our viral stocks and to ensure that the human Ad5 would infect ruminant cells, a bovine mammary epithelial cell line, BME-UV clone E-T2 (Zavizion et al., In Vitro Cell Dev. Biol. Anim. 32:138–148, 1996) was exposed to Av1LacZ4 (10 pfu/cell). After 48 hours, the cells were fixed and stained for β-galactosidase activity using the X-Gal reagent. The infection was successful (FIG. 7E).

C. Infection of the Goat Mammary Gland In Vivo

Goats were exposed to Av1LacZ4 to evaluate the ability of the human adenovirus to infect the ruminant mammary gland in vivo. Two mature, virgin, and three multiparous goats, which had been non-lactating for three months, were infused with the LacZ containing adenovirus. One teat of each goat was infused with 1 ml of a solution (10 mM Tris pH 7.4, 1 mM $MgCl_2$, 10% glycerol) containing Av1LacZ4 ($1.9 \times 10^{10}$ pfu/ml). The contralateral teat acted as a control being infused with vehicle. A similar set of infusions was administered 48 hours later but the concentration of virus was reduced to 0.6 pfu/ml. The animals were euthanized 24 hours later.

Teat tissue and mammary tissue samples adjoining the base of the teat were fixed in 2% paraformaldehyde-020. % glutaraldehyde and processed for detection of β-galactosidase activity (Furth et al., Molecular Biotechnology, 4:121–127, 1995). Intense blue staining of the entire lining of the teat canal was observed (FIG. 7A). Histological sections revealed that the infection was limited to the luminal cell layer (FIG. 7C). Mammary tissues were also infected (FIG. 7B).

Primary cultures of mammary tissues were prepared by collagenase digestion and plating on plastic culture dishes. After 24 hours incubation in DMEM containing 10% FBS in a 5% $CO_2$ atmosphere, the cultures were fixed and stained with X-Gal. Infected mammary epithelial cells were observed (FIG. 7D). There was no staining visible in tissues or cells from vehicle infused glands.

D. Characterization of Adenoviral-Mediated Transfection of the Goat Mammary Gland In order to continue to explore adenoviral transfection of the goat mammary gland, the β-galactosidase-containing adenovirus Av1LacZ4 is used. These studies are conducted with two, non-lactating multiparous goats treated similarly to the experiment described above. First, the dose response characteristics using a single infusion of adenovirus is explored. Goats are infected with a single, 1 ml infusions of $1.0 \times 10^{11}$, $1.0 \times 10^{10}$, $1.0 \times 10^9$ and $1.0 \times 10^8$ pfu/ml. Contralateral glands receive vehicle alone. These doses are based upon previous results. Mammary secretions are obtained prior to, and at, 24 hours and 48 hours post-infusion. The goats are euthanized 48 hours post-infusion. Evaluation of the infections includes monitoring animal health (temperature, respiration, rumination, and post-mortem evaluation) and determining SCC and the presence of bacterial infection.

Transfection is evaluated by staining teat and mammary tissues with X-gal reagent and subsequently evaluating them grossly and microscopically. Histopathology is also evaluated. Infusions of $1.9 \times 10^{10}$ and $0.6 \times 10^{10}$ pfu/ml are administered 72 hours and 24 hours prior to euthanasia, respectively. A minor inflammatory response may develop as evidenced by fluid accumulation in the gland and an elevation in somatic cell count. Rectal temperatures are monitored. Secretions are examined for bacterial contamination. This characterization allows determination of a lower dose of adenovirus that will ameliorate these symptoms, and yet still provide adequate transfection.

E. Adenoviral-Based Transfection of the Goat Mammary Gland with an Engineered Lysostaphin Construct.

Adenoviral-based transfection of the goat mammary gland in vivo has been undertaken as described for the Av1LacZ4 infections. Each of two multiparous non-lactating goats were infected in one gland by intramammary teat infusion with the lysostaphin-containing adenovirus. The contralateral gland was infused with the LacZ-containing adenovirus. The goats were euthanized 48 hours post-infusion. Mammary secretions were collected prior to infusion, and at 24 hours and 48 hours post-infusion. Secretions and tissues from the glands were processed as previously described with additional measurements for lysostaphin production and activity as follows.

Secretions from the glands and extracts prepared from tissue fragments were assayed for immunoreactive lysostaphin using Western blot and an ELISA assays (Kerr et al., Nat. Biotechnology (January, 2001) 19(1):66–70). Prior to performing the assays, sample infranatants previously described with additional measurements for lysostaphin production and activity as follows.

Secretions from the glands and extracts prepared from tissue fragments were assayed for immunoreactive lysostaphin using Western blot and an ELISA assays (Kerr et al., *Nat. Biotechnology* (January, 2001) 19(1):66–70). Prior to performing the assays, sample infranatants were prepared by two sequential centrifugation steps (15 min, 12,000 g, 4°) in which the fluid between the fat layer and pelletable protein and debris was harvested. All secretions were normalized based upon total protein content, determined by a modification of the Lowry method (Nerurkar et al., "Quantification of selected intracellular and secreted hydrolyses of macro phages." In *Manual of Macrophage Mehtodoloogy*. H. B. Herscowitz, et al., eds. (New York: Marcel Dekker, Inc.) pp. 229–246, 1981). Recovery of standard lysostaphin added to samples prior to processing was determined. At 48 hours post-infusion, the secretions collected from the two glands infused with the lysostaphin adenovirus contained 860 ng/ml and 1100 ng/ml, respectively, of lysostaphin. No lysostaphin was detected in the secretions from the contralateral glands infused with the lacZ-adenovirus.

Lysostaphin production is also evaluated in tissue sections processed for immunohisto-chemistry using our rabbit polyclonal antibody to lysostaphin. Immunohistochemical techniques are currently available. Briefly, formalin fixed tissue is embedded in paraffin, and sectioned (6 µm) by the UVM histology core facility. Slides are then deparaffinized and rehydrated. Endogenous peroxidases are blocked by a 10 min incubation with 0.3% hydrogen peroxide in methanol. Non-specific protein binding is blocked with a 30 min incubation in 10% normal goat serum in 1% BSA-PBS. Sections are incubated for 60 min with 10 µg/ml of rabbit polyclonal antibody generated against lysostaphin. Bound antibody is detected with biotinylated goat anti-rabbit IgG (Vector Laboratories, Burlingame, Calif.) subsequently coupled to streptavidin-peroxidase. The chromogen, amino ethyl carbazole (AEC) and the substrate (0.6% peroxide) are next added to the sections, allowing the development of a red color (Zymed Laboratories, San Francisco, Calif.). Negative controls are incubated with the primary antibody in the presence of a 100 fold excess of a lysostaphin. Av1LacZ4, the other with the lysostaphin containing adenovirus. Initial dose response experiments, conducted with two goats/dose, are undertaken to evaluate transfection during lactation. These experiments are 48 hours in duration. Subsequent longer duration experiments are conducted with a dose determined from previous experiments.

Example 3

Adenovirus Mediated Expression of Lysostaphin
A. Construction of Adenoviruses Containing Lysostaphin Genes GTI supplied start up quantities of an E3 region deletion mutant (AD5-dl327) of the AD5 adenovirus and the shuttle plasmid pAvS6 (Smith et. al., supra) that was used to construct the recombinant adenoviruses carrying the lysostaphin gene. The Not I-Kpn I fragment of the shuttle plasmid contains the inverted terminal repeat and encapsidation signal from the left end of AD5-dl327, the RSV promoter, a multi cloning region for insertion of the gene of interest, the SV40 Poly (A+) signal, and Ad5 sequences from nucleotide 3328 to 6246 that serve as a homologous recombination region.

Two shuttle plasmids were constructed. One, named pAvS6-preprolys, was constructed by inserting the 1.5 Kb modified lysostaphin gene from pCMLEM (Williamson et al., 1994) into the pAvS6 shuttle vector. This modified lysostaphin gene contained a Kozak region linked to the preprolysostaphin gene. The other, called pAvS6-hGH-Lys-ΔGLY1-ΔGLY2, contained the human growth hormone signal peptide linked to the modified lysostaphin construct, which was obtained from pCMV-hGH-Lys-ΔGLY1-ΔGLY2.

The shuttle plasmids pAvS6-preprolys and pAvS6-hGH-Lys-ΔGLY1-ΔGLY2 were independently used to generate two recombinant adenoviruses: Ad-preprolys and Ad-hGH-Lys-ΔGLY1-ΔGLY2, respectively. The recombinant viruses were constructed by co-transfection of the linearized shuttle plasmids with the ClaI fragment of Ad5-dl327 into 293 cells. Resulting plaques were purified. Insertion of the lysostaphin genes into the viral genomes was confirmed by polymerase chain reaction.

B. Evaluation of Lysostaphin Production by COS-7 Cells Infected with Ad-Preprolys Near confluent cultures of COS-7 cells were exposed to a cleared cell lysate from 293 cells that had been infected with Ad-preprolys to evaluate lysostaphin production. Samples of culture media and cell extracts were prepared from the infected COS-7 cells 48 hours after infection. Lysostaphin production was evaluated by an SDS-PAGE—Western blotting technique using a rabbit polyclonal antibody to lysostaphin (FIG. 3). The antibody was prepared for us by R. Sargent Inc. (Ramona, Calif.) using affinity purified lysostaphin (Sigma L-4402). Samples (50 µl) were denatured by boiling in the presence of a β-mercaptoethanol-containing loading buffer and electrophoresed through a 1.5 mm thick, 12% polyacrylamide gel for 4 hours (Protean II apparatus; Bio-Rad). Proteins were then transferred to nitrocellulose for immunodetection. Bound anti-lysostaphin antibody was detected with an alkaline phosphatase-linked second antibody (Sigma) and BCIP/NBT reagent (Bio-Rad). Cell extract from Ad-preprolys infected COS-7 cells contained a detectable quantity of immunoreactive lysostaphin that migrated with an apparent molecular weight of ≈90 Kd (FIG. 3, lane 10). This molecular mass is very similar to that previously observed by Williamson et al. (supra) (1994) following introduction of a similar lysostaphin construct using a plasmid based calcium phosphate transfection protocol. The protein is most likely preprolysostaphin. Mature lysostaphin migrates with an apparent MW of ≈28 Kd (FIG. 3, lanes 7, 8). The lysostaphin derived from Ad-preprolys infected COS-7 cells was apparently not secreted, as it was not detectable in the corresponding media sample (FIG. 3, lane 11). No bioactivity was detected in media or cell extracts from Ad-preprolys infected COS-7 cells.

C. Evaluation of Lysostaphin Production by 293 Cells Infected with Ad-hGH-Lys-ΔGLY1-ΔGLY2

Lysis of *S. aureus* (M60) by bioactive lysostaphin produced by 293 cells infected with Ad-hGH-Lys-ΔGLY1-ΔGLY2 was evaluated by plate assay. Samples (60 ul) or standards (15 ul) were added to a LB agar plate freshly streaked with *S. aureus*. Results were evaluated following a 12 hour incubation at 37°. Lysostaphin standards were prepared in media. The concentrations were 3 ng/ul, 30 ng/ul and 100 ng/ul. Inhibition of S. aureus growth was observed by the standard preparations and by culture media obtained from 293 cell cultures that had been infected with Ad-hGH-Lys-ΔGLY1-ΔGLY2. These results are illustrated in FIG. 1.

Example 4

Production and Evaluation of Transgenic Mice Incorporating the Lysostaphin Gene Under Control of a Mammary Specific Promoter This model allows assessment of the functionality of the transgene when incorporated into the genome of an animal, determination of toxicity of the transgenic protein to the lactating mammary gland, and assessment of the effects of the transgene on milk production. The antibacterial properties of milk from these animals can also be measured. A variety of mammary gland and lactation specific promoter regions may be used to direct expression of the lysostaphin gene to the lactating mammary gland. These include, but are not limited to, the regulatory sequences of the casein genes, whey acidic protein, and lactoglobulin. We chose to use the β-lactoglobulin regulatory sequence.

A. Lysostaphin Expression in Milk

The 4.2 Kb 5'-flanking (promoter) region and the 2.1 Kb of the 3-flanking region of the ovine β-lactoglobulin (BLG) gene (pBJ41) were obtained from Dr. A. J. Clark (Roslin Institute, UK). These components have been used to direct the production of mg/ml concentrations of foreign proteins into the milk of mice (Archibald et al., *Proc. Natl. Acad. Sci. USA* 87,5178–5182, 1990) and sheep (Wright et al., *Biotechnology* 9, 830–834, 1991). The 1.4 Kb modified lysostaphin gene containing the hGH signal peptide was excised from pSec-Lys-Gln2 and inserted into pBJ41 between the 5'-and 3'-components of the BLG gene. The entire 7.7 Kb fusion gene (BLG-Sec-Lys-Gln2) was then excised and purified for microinjection. Nine founder transgenic mice were produced in the laboratory of Dr. R. J. Wall (USDA-ARS-GEML; Beltsville, Md.) using standard techniques. Five lines of mice have now been established. These mice appear normal, are fertile, and are able to raise offspring. To date, milk has been obtained from F1 mice representing three of the lines. The milk was collected on day 10 of lactation (Maga et al., *J. Dairy Sci.* 78: 2645–2652, 1995). The milk samples were immediately frozen (–80) and then shipped to our laboratory on dry ice.

Figure 9:
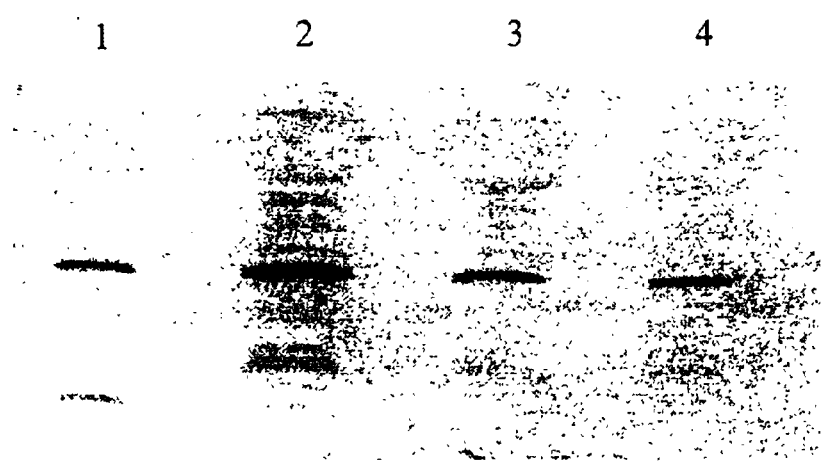
FIG. 9 shows a Western blot of lysostaphin in milk from transgenic mice containing the BLG-Sec-Lys-Gln2 construct. Lane 1 contains 10 µl of lysostaphin standard (Sigmas 1 µg/µl) in PBS-1% BSA. Lanes 2–4 contain milk samples from three different transgenic mice (10 µl milk diluted 1:10 in PBS-1% BSA). Lysostaphin was not detected in non-transgenic mouse milk.

Milk was analyzed for lysostaphin immunoreactivity as described for cell culture experiments. Prior to analysis milk samples were diluted (1:10) in PBS containing 0.5% BSA, then defatted by centrifugation (15 min, 4, 10,000 g). Western blot analysis of milk from three different BLG-Sec-Lys-Gln2-transgenic mice (#16797, #16796, #16775) revealed a very intense lysostaphin band (FIG. 9). The migration distance appears identical to the lysostaphin standard.

Figure 10:
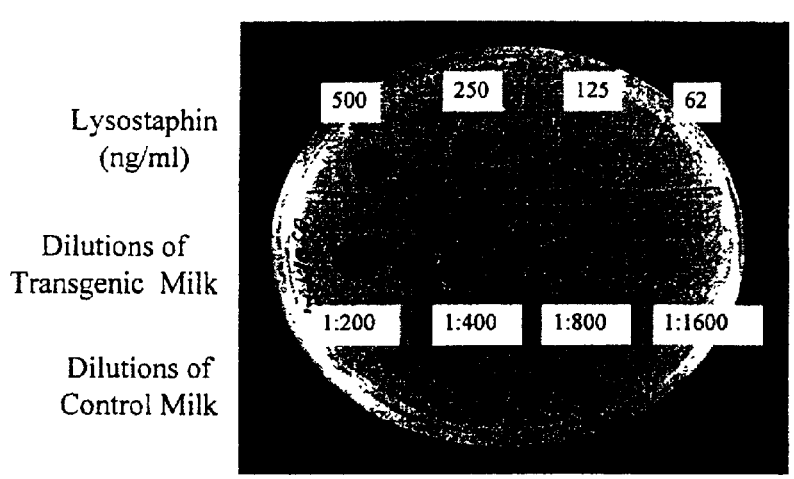
FIG. 10 shows a bacterial plate assay for lysostaphin bioactivity in mouse milk. Milk samples or lysostaphin standards (15 µl) were spotted onto a freshly plated lawn of S. aureus and lytic zones were observed after overnight incubation. Top row, left to right: bacterially derived lysostaphin (Sigma 500, 250, 125, 62 ng/ml in PBS-1% BSA) middle row, left to right: skim milk from a BLG-Sec-Lys-Gln2 transgenic mouse (#16755) diluted 1:200, 1:400, 1:800 or 1:1600 in PBS-1% BSA. Bottom row, left to right: skim milk from a non-transgenic mouse diluted 1:200, 1:400, 1:800 1:1600 in PBS-1% BSA.
Figure 19:
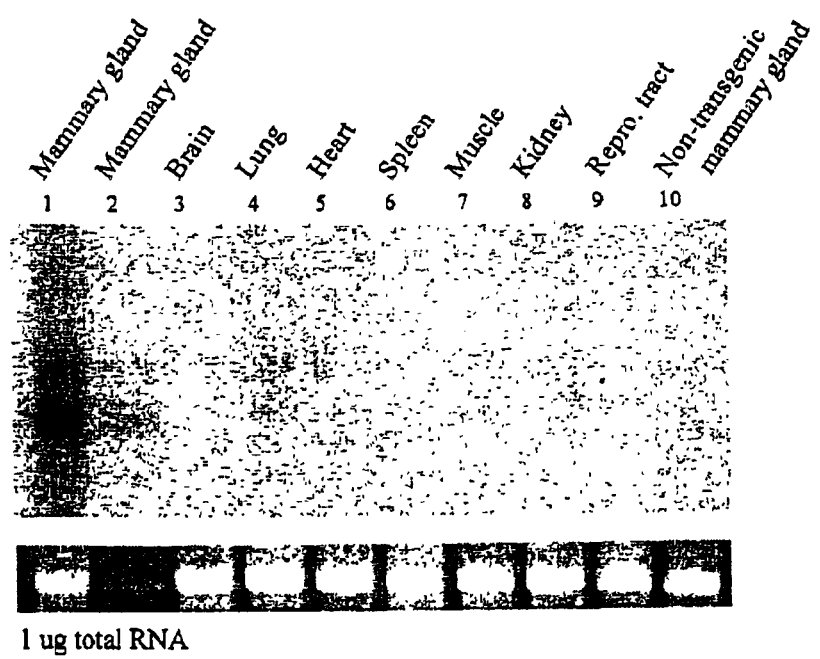
FIG. 19 is a Northern blot of RNA from various tissues of a transgenic mouse showing almost complete mammary specificity of lysostaphin expression.

Milk from another BLG-Sec-Lys-Gln2-transgenic mouse (#16755) contained substantial staphylolytic bioactivity (FIG. 10). The lytic zones that developed from a dilution series of milk indicated that a 1:1,600 dilution of milk contained an amount of bioactivity equivalent to between 125 ng/ml and 250 ng/ml of lysostaphin standard (Sigma).

B. In Vivo Lysostaphin Activity in Mice

The use of transgenesis to direct mammary gland expression of foreign protein in the mouse was first reported in 1987 by Gordon et al. (*Biotechnology* 5:1183–1187). This technology spread to transgenic pigs (Wall et al., *Proc. Natl. Acad. Sci. USA* (1991) 88:1696–1700), sheep (Wright et al., *Biotechnology* (1991) 9:830–834), goats (Ebert et al., *Biotechnology* (1991) 9:835-838), and cattle (Krimpenfort et al., *Biotechnology* (1991) 844–847). The present example demonstrates that secreting a modified, biologically active form of lysostaphin in milk protects transgenic mice against S. aureus infection. These results demonstrate that a genetic engineering approach may be an effective strategy for combating mastitis, the single most problematic disease problem in dairy cattle industry.

Modification of the bacterial lysostaphin gene for eukaryotic expression of bioactive $Gln^{125,232}$-lysostaphin was carried out as described above. Briefly, the Sec-Gln-Lys construct was inserted between the 4.2 Kb 5'-flanking region and the 2.1 Kb 3' flanking region of the ovine β-approach may be an effective strategy for combating mastitis, the single most problematic disease problem in dairy cattle industry.

Modification of the bacterial lysostaphin gene for eukaryotic expression of bioactive $Gln^{125,232}$-lysostaphin was carried out as described above. Briefly, the Sec-Gln-Lys construct was inserted between the 4.2 Kb 5'-flanking region and the 2.1 Kb 3' flanking region of the ovine β-lactoglobulin gene. The entire 7.7 Kb BLG-lysostaphin (BLG-Lys) fusion gene, was then used to generate transgenic mice. Eight potential founders carrying the BLG-Lys construct were identified by Southern blot analysis. Two of these animals did not transmit their transgene to progeny. Daughters of three other founders expressed lysostaphin in their milk at a very low concentration (<20 μg/ml) and therefore these lines were not further evaluated. Offspring founder 16535 produced lysostaphin at 75 μg/ml of milk and was designated as the low expressing line. The BLG-Lys transgene integrated at two loci in the genome of founder 16654 segregated independently in his progeny. The segregation of one of the sites resulted in the generation of a sub line expressing 150 μg/ml of milk which was designated the medium expressing line. The other site produced a sub-line expressing approximately 1 mg/ml of milk and was designated as the high expressing line.

Milk from these mice contains substantial staphylolytic activity, as detected by a bacterial plate assay. Although the eukaryotically produced $Gln^{125,232}$-lysostpahin appears to be 5- to 10-fold less potent than bacterially derived lysostaphin, as shown below, it is potent enough to inhibit S. aureus infection of mouse mammary tissue in vivo. The difference in biological activity was demonstrated by comparison of lytic zones in a lawn of S. aureus resulting from application of bacterial lysostaphin standards or dilutions of a milk sample from a high expressing line transgenic mouse (FIG. 18). The milk sample contained 1.3 mg/ml immunoreactive lysostaphin, yet the lytic zone developed from a 1:1600 dilution of this sample, which would contain approximately 800 ng/ml, was similar to that produced by a solution containing 125 ng/ml bacterial lysostaphin. In contrast, milk from non-transgenic mice does not contain staphylolytic activity.

Susceptibility to mastitis following intramammary infection was evaluated with a murine model previously developed to demonstrate the efficacy of lysostaphin as a mastitis therapeutic (Bramley et al., *Res. Vet. Sci.*, (1990) 49:120–121). Experimental mastitis was produced by intramammary inoculation as described by Bramley et al. (*Res. Vet. Sci.*, (1990) 49:120–121) and Chandler, R. L. (*J. Med. Microbiol.* (1970) 3:273–282). In the experimental model, two abdominal mammary glands of mice were inoculated with *S. aureus* ($10^4$ cfu/50 µl PBS) on the tenth day of lactation. To put this dose into perspective, cows are often experimentally challenged with less than 1000 cfu (Oldman and Daley, *J. Dairy Sci.* (1991) 74;4175–4182; Watson, D. L., *Res. Vet. Sci.* (1992) 53:346–353). Pups were removed and inoculum delivered to anesthetized mice via the teat canal with a 100 µl Hamilton syringe fitted with a 34 g blunt needle. This dose of bacteria is sufficient to cause severe infection within 24 hours, at which point the mice are euthanized and mammary homogenates prepared. Mice were maintained on an analgesic (buprenorphine) during the incubation period. Viable *S. aureus* in the homogenate were determined by plating out a dilution series on blood agar plates, incubating for 24 hours, then enumerating colonies. Colony morphology and hemolytic clearing were used as indicators of *S. aureus*.

The dose of *S. aureus* administered was sufficient to cause active intramammary infection in all infused glands of non-transgenic mice, see Table 1 below. In contrast, glands of the high expressing line BLG-Lys transgenic mice were completely resistant to infection, as were approximately 40% of glands from the medium and low expression lines. Further, 17 of 22 control glands were classified as severely infected, based on *S. aureus* recovery. These glands had obvious visible signs of trauma, such as bloody, serous exudate surrounding the mammary glands. In marked contrast, the glands of transgenic mice never exhibited visual signs of infection, even in those glands from the low and medium expressing lines that contained viable *S. aureus*. In Table 1, the degree of resistance to infection was related to the amount of lysostaphin in the glands.

Table 1.

Infection status of mouse mammary glands 24 hours after intramammary challenge with *S. aureus*. Glands were infused on day 10 of lactation with *S. aureus* ($10^4$ cfu/50 ml/gland). Infection status is based on number of *S. aureus* (cfu) recovered from each gland 24 hours post-infusion (Wilson et al., *J. Dairy Sci.* (1997) 80:2592–2598). Each abdominal mammary gland (L4, R4) was homogenized in 2 ml PBS.

| Line | Glands Infused | Glands Infected | Infection Status (cfu/gland) | | | | Lysostaphin in mammary gland (ug/ml) Mean ± s.e. |
| --- | --- | --- | --- | --- | --- | --- | --- |
| | | | Severe ($>10^8$) | Moderate ($10^5$ to $10^8$) | Mild ($10^2$ to $10^5$) | Clean ($<10^2$) | |
| Non-transgenic | 22 | 22 | 17 | 4 | 1 | 0 | 0 |
| BLG-Lys Low | 8 | 5 | 0 | 4 | 1 | 3 | 1.5 ± 0.02 |
| BLG-Lys Medium | 6 | 3 | 0 | 3 | 0 | 3 | 6.0 ± 1.1 |
| BLG-Lys High | 8 | 0 | 0 | 0 | 0 | 8 | 50.3 ± 9.7 |

To summarize, this example demonstrates that transgenic production of lysostaphin by lactating mammary gland will confer substantial resistance to staphylococcal mastitis. Furthermore, the staphylolytic enzyme does not appear to affect mammary integrity, milk quality, or ability to produce fermented dairy products. Mice from the highest expressing line were completely resistant to experimental challenge, while mice from the medium and low expressing lines had clearly enhanced resistance. Viable *S. aureus* were recovered from approximately 60% of challenged glands from the low and medium expressing transgenic mice. However, none of these glands were severely or visibly infected, as were 77% of non-transgenic glands.

Example 5

Transgenic Ruminants

The present invention provides transgenic dairy cows containing a modified lysostaphin gene, although the cost and duration of such an endeavor necessitates preliminary experiments using the much less expensive, and more rapid, transgenic mouse model.

A. Production of Non-Rodent Transgenic Animals

Procedures for the production of transgenic non-rodent mammals and other animals have been discussed by others (see Houdebine and Chourrout, supra; Pursel et al., *Science* 244:1281, 1989; and Simms et al., *Bio/Technology*, 6:179, 1988). Such procedures can be applied to an altered gene of the present invention to produce transgenic dairy cows expressing lysostaphin (see Krimpenfort et al., *Biotechnology*, 9:844–847, 1991, incorporated herein by reference). If expression is desirably limited to mammary tissues, a mammary-specific promoter may be employed.

Other Embodiments

One of ordinary skill in the art will readily recognize that the foregoing represents merely a detailed description of certain preferred embodiments of the present invention. Various modifications and alterations of the genes and uses thereof described above can readily be achieved using expertise available in the art, and are within the scope of the following claims.

All references cited herein are hereby incorporated by reference.

What is claimed is:

1. A non-human transgenic mammal whose genome contains a transgene, wherein the transgene comprises, in operable association:
   (i) a mammary gland specific promoter;
   (ii) a DNA portion having a sequence that encodes a secretion signal sequence functional in mammary gland secretory cells; and
   (iii) a DNA portion having a sequence that encodes an active lysostaphin protein,
   wherein a milk-producing transgenic non-human mammal having the genotype of the transgenic non-human mammal expresses the transgene in mammary gland secretory cells such that the active lysostaphin protein is detectable in milk of the milk-producing transgenic non-human mammal.

2. The non-human transgenic mammal of claim 1, wherein the transgene comprises a eukaryotic start codon located 3' to the promoter, and wherein the transgene further comprises a Kozak expression start site consensus sequence located 3' to the promoter and including the eukaryotic start codon.

3. The non-human transgenic mammal of claim 1, wherein the DNA portion having a sequence that encodes an active lysostaphin protein includes one or more alterations with respect to the naturally occurring version of lysostaphin, wherein one or more of the alterations disrupts a mammalian post-translational processing event.

4. The non-human transgenic mammal of claim 1, wherein one or more of the alterations disrupts a glycosylation event that would otherwise occur in mammalian cells.

5. A non-human transgenic mammal whose genome contain a transgene, wherein the transgene comprises, in operable association:
   (i) a promoter selected from the group consisting of: a β-lactoglobulin promoter, an α-lactalbumin promoter; a casein promoter; a whey acidic protein promoter;
   (ii) a DNA portion having a sequence that encodes a secretion signal sequence functional in mammary gland secretory cells; and
   (iii) a DNA portion having a sequence that encodes an active lysostaphin protein,
   wherein a milk-producing non-human transgenic mammal having the genotype of the transgenic non-human mammal expresses the transgene in mammary gland secretory cells such that the active lysostaphin protein is detectable in milk of the milk-producing non-human transgenic mammal.

6. The non-human transgenic mammal of claim 5, wherein the promoter is a β-lactoglobulin promoter.

7. The non-human transgenic mammal of claim 6, wherein the transgene comprises 4.2 kB of the 5' regulatory region of the ovine β-lactoglobulin gene.

8. The non-human transgenic mammal of claim 6, wherein the transgene comprises 2.0 kB of the 3' untranslated region of the ovine β-lactoglobulin gene.

9. The non-human transgenic mammal of claim 5, wherein the DNA portion having a sequence that encodes an active lysostaphin protein includes one or more alterations with respect to the naturally occurring version of lysostaphin, wherein one or more of the alterations disrupts a mammalian post-translational processing event.

10. The non-human transgenic mammal of claim 5, wherein one or more of the alterations disrupts a glycosylation event that would otherwise occur in mammalian cells.

11. A non-human transgenic manunal whose genome contains a transgene, wherein the transgene comprises, in operable association:
    (i) a promoter that is functional in mammary gland secretory cells;
    (ii) a DNA portion having a sequence that encodes a secretion signal sequence functional in mammary gland secretory cells; and
    (iii) a DNA portion having a sequence that encodes an active lysostaphin protein,
    wherein a milk-producing non-human transgenic mammal having the genotype of the non-human transgenic mammal expresses the transgene in mammary gland secretory cells such that the active lysostaphin protein is detectable in milk of the milk-producing non-human transgenic mammal.

12. The non-human transgenic mammal of claim 11, wherein the transgene comprises a eukaryotic start codon located 3' to the promoter, and wherein the transgene further comprises a Kozak expression start site consensus sequence located 3' to the promoter and including the eukaryotic start codon.

13. The non-human transgenic mammal of claim 11, wherein the DNA portion having a sequence that encodes an active lysostaphin protein includes one or more alterations with respect to the naturally occurring version of lysostaphin, wherein one or more of the alterations disrupts a mammalian post-translational processing event.

14. The non-human transgenic mammal of claim 11, wherein one or more of the alterations disrupts a glycosylation event that would otherwise occur in mammalian cells.

* * * * *

SEQUENCE LISTING

<160> NUMBER OF SEQ ID NOS: 10

<210> SEQ ID NO 1
<211> LENGTH: 1486
<212> TYPE: DNA
<213> ORGANISM: Staphylococcus simulans

<400> SEQUENCE: 1

```
ccggaactct tgaatgttta gttttgaaaa ttccaaaaaa aaacctacct tcttaatatt    60
gattcatatt atttaacac aatcagttag aatttcaaaa atcttaaagt caatttttga   120
gtgtgtttgt atatttcatc aaaatcaatc aatattattt tactttcttc atcgttaaaa   180
aatgtaatat ttataaaaat atgctattct cataaatgta ataataaatt aggaggtatt   240
aaggttgaag aaaacaaaaa acaattatta tacgagacct ttagctattg gactgagtac   300
atttgcctta gcatctattg tttatggagg gattcaaaat gaaacacatg cttctgaaaa   360
aagtaatatg gatgtttcaa aaaagtagc tgaagtagag acttcaaaag ccccagtaga   420
aaatacagct gaagtagaga cttcaaaagc tccagtagaa atacagctg aagtagagac   480
ttcaaaagct ccagtagaaa atacagctga agtagagact tcaaaagctc cagtagaaaa   540
tacagctgaa gtagagactt caaaagctcc ggtagaaaat acagctgaag tagagacttc   600
aaaagcccca gtagaaaata cagctgaagt agagacttca aaagccctgg ttcaaaatag   660
aacagcttta agagctgcaa cacatgaaca ttcagcacaa tggttgaata attacaaaaa   720
aggatatggt tacggtcctt atccattagg tataaatggc ggtatgcact acggagttga   780
ttttttatg aatattggaa caccagtaaa agctatttca gcggaaaaa tagttgaagc   840
tggttggagt aattacggag gaggtaatca aataggtctt attgaaaatg atggagtgca   900
tagacaatgg tatatgcatc taagtaaaata gtaggagatt gtaggagatt atgtcaaagc   960
tggtcaaata atcggttggt ctggaagcac tggttattct acagcaccac atttacactt  1020
ccaaagaatg gttaattcat ttcaaattc aactgcccaa gatccaatgc ctttcttaaa  1080
gagcgcagga tatggaaaag caggtggtac agtaactcca acgccgaata caggttggaa  1140
aacaaacaaa tatggcacac tatataaatc agagtcagct agcttcacac ctaatacaga  1200
tataataaca agaacgactg gtccatttag aagcatgccg cagtcaggag tcttaaaagc  1260
aggtcaaaca attcattatg atgaagtgat gaaacaagac ggtcatgttt gggtaggtta  1320
tacaggtaac agtggccaac gtatttactt gcctgtaaga acatggaata aatctactaa  1380
tactttaggt gttctttggg gaactataaa gtgagcgcgc tttttataaa cttatatgat  1440
aattagagca aataaaaatt ttttctcatt cctaaagttg aagctt              1486
```

<210> SEQ ID NO 2
<211> LENGTH: 388
<212> TYPE: PRT
<213> ORGANISM: Staphyloccus simulans

<400> SEQUENCE: 2

```
Met Lys Lys Thr Lys Asn Asn Tyr Tyr Thr Arg Pro Leu Ala Ile Gly
  1               5                  10                  15

Leu Ser Thr Phe Ala Leu Ala Ser Ile Val Tyr Gly Gly Ile Gln Asn
                 20                  25                  30

Glu Thr His Ala Ser Glu Lys Ser Asn Met Asp Val Ser Lys Lys Val
             35                  40                  45
```

| | | | | | | | | | | | |
|---|---|---|---|---|---|---|---|---|---|---|---|
|Ala|Glu|Val|Glu|Thr|Ser|Lys|Ala|Pro|Val|Glu|Asn|Thr|Ala|Glu|Val|
| |50| | | | |55| | | |60| | | | | |

Ala Glu Val Glu Thr Ser Lys Ala Pro Val Glu Asn Thr Ala Glu Val
         50                  55                  60

Glu Thr Ser Lys Ala Pro Val Glu Asn Thr Ala Glu Val Glu Thr Ser
 65                  70                  75                  80

Lys Ala Pro Val Glu Asn Thr Ala Glu Val Glu Thr Ser Lys Ala Pro
                 85                  90                  95

Val Glu Asn Thr Ala Glu Val Glu Thr Ser Lys Ala Pro Val Glu Asn
            100                 105                 110

Thr Ala Glu Val Glu Thr Ser Lys Ala Pro Val Glu Asn Thr Ala Glu
        115                 120                 125

Val Glu Thr Ser Lys Ala Leu Val Gln Asn Arg Thr Ala Leu Arg Ala
    130                 135                 140

Ala Thr His Glu His Ser Gln Trp Leu Asn Asn Tyr Lys Lys Gly Tyr
145                 150                 155                 160

Gly Tyr Gly Pro Tyr Pro Leu Gly Ile Asn Gly Gly Met His Tyr Gly
                165                 170                 175

Val Asp Glu Phe Met Asn Ile Gly Thr Pro Val Lys Ala Ile Ser Ser
            180                 185                 190

Gly Lys Ile Val Glu Ala Gly Trp Ser Asn Tyr Gly Gly Gly Asn Gln
        195                 200                 205

Ile Gly Leu Ile Glu Asn Asp Gly Val His Arg Gln Glu Tyr Met His
    210                 215                 220

Leu Ser Lys Tyr Asn Val Lys Val Gly Asp Tyr Val Lys Ala Gly Gln
225                 230                 235                 240

Ile Ile Gly Trp Ser Gly Ser Thr Gly Tyr Ser Thr Ala Pro His Leu
                245                 250                 255

His Phe Gln Arg Met Val Asn Ser Phe Ser Asn Ser Thr Ala Gln Asp
            260                 265                 270

Pro Met Pro Phe Leu Lys Ala Ser Gly Tyr Gly Lys Ala Gly Gly Thr
        275                 280                 285

Val Thr Pro Thr Pro Asn Thr Gly Trp Lys Thr Asn Lys Tyr Gly Thr
    290                 295                 300

Leu Tyr Lys Ser Glu Ser Ala Ser Phe Thr Pro Asn Thr Asp Ile Ile
305                 310                 315                 320

Thr Arg Thr Thr Gly Pro Phe Arg Ser Met Pro Gln Ser Gly Val Leu
                325                 330                 335

Lys Ala Gly Gln Thr Ile His Tyr Asp Glu Val Met Lys Gln Asp Gly
            340                 345                 350

His Val Trp Val Gly Tyr Thr Gly Asn Ser Gly Gln Arg Ile Tyr Leu
        355                 360                 365

Pro Val Arg Thr Trp Asn Lys Ser Thr Asn Thr Leu Gly Val Leu Trp
    370                 375                 380

Gly Thr Ile Lys
385

<210> SEQ ID NO 3
<211> LENGTH: 741
<212> TYPE: DNA
<213> ORGANISM: Staphylococcus simulans

<400> SEQUENCE: 3
gccgcaacac atgaacattc agcacaatgg ttgaataatt acaaaaaagg atatggttac    60
ggcccttatc cattaggtat aaatggcggt atgcactacg gagttgattt ttttatgaat   120
attggaacac cagtaaaagc tatttcaagc ggaaaaatag ttgaagctgg ttggagtaat   180

-continued

| | |
|---|---|
| tacggaggag gtaatcaaat aggtcttatt gaaaatgatg gagtgcatag acaatggtat | 240 |
| atgcatctaa gtaaatataa tgttaaagta ggagattatg tcaaagctgg tcaaataatc | 300 |
| ggttggtctg gaagcactgg ttattctaca gcaccacatt tacacttcca aagaatggtt | 360 |
| aactcatttt cacagtcaac tgcccaagat ccaatgcctt tcttaaagag cgcaggatat | 420 |
| ggaaaagcag gtggtacagt aactccaacg ccgaatacag gttggaaaac aaacaaatat | 480 |
| ggcacactat ataaatcaga gtcagctagc ttcacaccta atacagatat aataacaaga | 540 |
| acgactggtc catttagaag catgccgcag tcaggagtct aaaagcagg tcaaacaatt | 600 |
| cattatgatg aagtgatgaa acaagacggt catgtttggg taggttatac aggtaacagt | 660 |
| ggccaacgta tttacttgcc tgtgagaaca tggcagaagt ctactaatac tctgggtgtt | 720 |
| ctgtggggaa ctataaagtg a | 741 |

<210> SEQ ID NO 4
<211> LENGTH: 1520
<212> TYPE: DNA
<213> ORGANISM: Staphylococcus simulans

<400> SEQUENCE: 4

| | |
|---|---|
| tgtgtgcgtg ctcccattcg ttcatgctcg ccacgcgcac ggccgcgctt tgcgacgcga | 60 |
| tcgcgcaccg tgtgaaccgc attgaggaat ggccgttcgg caagcgcatg tacggcctcg | 120 |
| atttgaacgt gcgtcgcacg acagcgtcgc gcccgcggtc agagtccggc gcccgcggta | 180 |
| tacgacagc gatcgcggcg tccgccgatg acgaacggtc gtgcgcgtca gtcgcatgcg | 240 |
| ccgctcgccg ctggcgttcc ggcttcgcgg gcgcagcgcg gtccaccact cttcaaacgt | 300 |
| cttttctcggg agcagcatat gaagaagatt tccaaggcgg gactgggggct ggcgctggtg | 360 |
| tgcgcgctgg cgacgatcgg cggcaacgca gcgcgcaggg ccacggctca gcggcgagga | 420 |
| tctggtgtat tctacgacga gatgttcgac ttcgacatcg atgcgcatct ggccaagcat | 480 |
| gcgccgcatc tgcacaagca ctcggaagag atctcgcact gggccggcta cagcgggatc | 540 |
| agccgaagtg ttgatcgcgc tgatggagca gcagagcgcg cggtcacgcc aagcgcgcga | 600 |
| cgaatcgtcc gttcggcaag ctggcgcgcg ccgacggctt cggcgcgcag acccgcgagg | 660 |
| tcgcgctggc gctgcgcgag tcgctgtacg agcgcgatcc cgacgcgcca aggggccggt | 720 |
| gacgctggcc cgcgccaatc cgctgcaggc gctgttcgag cgttccggcg acaacgagcc | 780 |
| ggcggccgcg ctgcgcggcg acggcgagtt ccagctggtc tacggccgcc tgttcaacga | 840 |
| accgcgccag gccaaggcgg cttcggaccg cttcgccaag gccggcccgg acgtgcagcc | 900 |
| gtgtcgccca acggcctgct gcagttcccc ttcccgcgcg cgccagctg gcatgtcggc | 960 |
| ggcgcccaca ccaacaccgg ctcgggcaat tacccgatgt cgtcgctgga catgtcgcgc | 1020 |
| ggcggcggct ggggcagcaa ccagaacggc aactgggtgt cggcctcggc cgccggctcg | 1080 |
| ttcaagcgcc actcttcgtg cttcgcggag atcgtgcaca ccggcggctg gtcgacgacc | 1140 |
| tactaccacc tgatgaacat ccagtacaac accggcgcca acgtgtcgat gaacaccgcc | 1200 |
| atcgccaacc cggccaacac ccaggcgcag gcgctgtgca acgcgggcca gtcgaccggc | 1260 |
| ccgcacgagc attggtcgtt gaagcagaac ggcagcttct accacctcaa cggcacctac | 1320 |
| ctgtcgggct atcgcatcac cgcgaccggc agcagctatg acaccaactg cagccggttc | 1380 |
| tatctgacca agaacggcca gaactactgc tacggctatt acgtcaaccc gggcccgaac | 1440 |
| tgaggctcgc cgcgtgcgtt gcccgcgtcc tcaagcgccc cacgcgcggg gcgcgggcac | 1500 |

```
cggccgggtc aggtcgaatt                                                    1520
```

<210> SEQ ID NO 5
<211> LENGTH: 480
<212> TYPE: PRT
<213> ORGANISM: Staphylococcus simulans

<400> SEQUENCE: 5

| Met | Lys | Lys | Thr | Lys | Asn | Asn | Tyr | Tyr | Thr | Pro | Leu | Ala | Ile | Gly |
|---|---|---|---|---|---|---|---|---|---|---|---|---|---|---|
| 1 | | | | 5 | | | | | 10 | | | | | 15 |

Leu Ser Thr Phe Ala Leu Ala Ser Ile Val Tyr Gly Gly Ile Gln Asn
          20                  25                  30

Glu Thr His Ala Ser Glu Lys Ser Asn Met Asp Val Ser Lys Lys Val
              35                  40                  45

Ala Glu Val Glu Thr Ser Lys Pro Val Glu Asn Thr Ala Glu Val
 50                  55                  60

Glu Thr Ser Lys Ala Pro Val Glu Asn Thr Ala Glu Val Glu Thr Ser
 65                  70                  75                  80

Lys Ala Pro Val Glu Asn Thr Ala Glu Val Glu Thr Ser Lys Ala Pro
              85                  90                  95

Val Glu Asn Thr Ala Glu Val Glu Thr Ser Lys Ala Pro Val Glu Asn
            100                 105                 110

Thr Ala Glu Val Glu Thr Ser Lys Ala Pro Val Glu Asn Thr Ala Glu
        115                 120                 125

Val Glu Thr Ser Lys Ala Pro Val Glu Asn Thr Ala Glu Val Glu Thr
    130                 135                 140

Ser Lys Ala Pro Val Glu Asn Thr Ala Glu Val Glu Thr Ser Lys Ala
145                 150                 155                 160

Pro Val Glu Asn Thr Ala Glu Val Glu Thr Ser Lys Ala Pro Val Glu
                165                 170                 175

Asn Thr Ala Glu Val Glu Thr Ser Lys Ala Pro Val Glu Asn Thr Ala
            180                 185                 190

Glu Val Glu Thr Ser Lys Ala Pro Val Glu Asn Thr Ala Glu Val Glu
        195                 200                 205

Thr Ser Lys Ala Pro Val Glu Asn Thr Ala Glu Val Glu Thr Ser Lys
    210                 215                 220

Ala Leu Val Gln Asn Arg Thr Ala Leu Arg Ala Thr His Glu His
225                 230                 235                 240

Ser Ala Gln Trp Leu Asn Asn Tyr Lys Tyr Gly Tyr Gly Tyr Gly Pro
                245                 250                 255

Tyr Pro Leu Gly Ile Asn Gly Gly Ile His Tyr Gly Val Asp Phe Phe
            260                 265                 270

Met Asn Ile Gly Thr Pro Val Lys Ala Ile Ser Ser Gly Lys Ile Val
        275                 280                 285

Glu Ala Gly Trp Ser Asn Tyr Gly Gly Gly Asn Gln Ile Gly Leu Ile
    290                 295                 300

Glu Asn Asp Gly Val His Arg Gln Trp Tyr Met His Leu Ser Lys Tyr
305                 310                 315                 320

Asn Val Lys Val Gly Asp Tyr Val Lys Ala Gly Gln Ile Ile Gly Trp
                325                 330                 335

Ser Gly Ser Thr Gly Tyr Ser Thr Ala Pro His Leu His Phe Gln Arg
            340                 345                 350

Met Val Asn Ser Phe Ser Asn Ser Thr Ala Gln Asp Pro Met Pro Phe
        355                 360                 365

```
Leu Lys Ser Ala Gly Tyr Gly Lys Ala Gly Gly Thr Val Pro Thr
            370                 375                 380

Pro Asn Thr Gly Trp Lys Thr Asn Lys Tyr Gly Thr Leu Tyr Lys Ser
385                 390                 395                 400

Glu Ser Ala Ser Phe Thr Pro Asn Thr Asp Ile Ile Thr Arg Thr Thr
                    405                 410                 415

Gly Pro Phe Arg Ser Met Pro Gln Ser Gly Val Leu Lys Ala Gly Gln
            420                 425                 430

Thr Ile His Tyr Asp Glu Val Met Lys Gln Asp Gly His Val Trp Val
            435                 440                 445

Gly Tyr Thr Gly Asn Ser Gly Gln Arg Ile Tyr Leu Pro Val Arg Thr
450                 455                 460

Trp Asn Lys Ser Thr Asn Thr Leu Gly Val Leu Trp Gly Thr Ile Lys
465                 470                 475                 480

<210> SEQ ID NO 6
<211> LENGTH: 492
<212> TYPE: PRT
<213> ORGANISM: Achromobacter lyticus

<400> SEQUENCE: 6

Met Lys Lys Thr Lys Asn Asn Tyr Tyr Thr Arg Pro Leu Ala Ile Gly
1               5                   10                  15

Leu Ser Thr Phe Ala Leu Ala Ser Ile Val Tyr Gly Gly Ile Gln Asn
                20                  25                  30

Glu Thr His Ala Ser Glu Lys Ser Asn Met Asp Val Ser Lys Lys Val
            35                  40                  45

Ala Glu Val Glu Thr Ser Lys Ala Pro Val Glu Asn Thr Ala Glu Val
    50                  55                  60

Glu Thr Ser Lys Ala Pro Val Glu Asn Thr Ala Glu Val Glu Thr Ser
65                  70                  75                  80

Lys Ala Pro Val Glu Asn Thr Ala Glu Val Glu Thr Ser Lys Ala Pro
                85                  90                  95

Val Glu Asn Thr Ala Glu Val Glu Thr Ser Lys Ala Pro Val Glu Asn
            100                 105                 110

Thr Ala Glu Val Glu Thr Ser Lys Ala Pro Val Glu Asn Thr Ala Glu
        115                 120                 125

Val Glu Thr Ser Lys Ala Pro Val Glu Asn Thr Ala Glu Val Glu Thr
130                 135                 140

Ser Lys Ala Pro Val Glu Asn Thr Ala Glu Val Glu Thr Ser Lys Ala
145                 150                 155                 160

Pro Val Glu Asn Thr Ala Glu Val Glu Thr Ser Lys Ala Pro Val Glu
                165                 170                 175

Asn Thr Ala Glu Val Glu Thr Ser Lys Ala Pro Val Glu Asn Thr Ala
            180                 185                 190

Glu Val Glu Thr Ser Lys Ala Pro Val Glu Asn Thr Ala Glu Val Glu
        195                 200                 205

Thr Ser Lys Ala Pro Val Glu Asn Thr Ala Glu Val Glu Thr Ser Lys
    210                 215                 220

Ala Pro Val Glu Asn Thr Ala Glu Val Glu Thr Ser Lys Ala Leu Val
225                 230                 235                 240

Gln Arg Thr Ala Leu Arg Ala Ala Thr His Glu His Ser Ala Gln Trp
                245                 250                 255

Leu Asn Asn Tyr Lys Lys Gly Tyr Gly Tyr Gly Pro Tyr Pro Leu Gly
            260                 265                 270
```

-continued

```
Ile Asn Gly Gly Met His Tyr Gly Val Asp Phe Phe Met Asn Ile Gly
        275                 280                 285

Thr Pro Val Lys Ala Ile Ser Ser Gly Lys Ile Val Glu Ala Gly Trp
    290                 295                 300

Ser Asn Tyr Gly Gly Gly Asn Gln Ile Gly Leu Ile Glu Asn Asp Gly
305                 310                 315                 320

Val His Arg Gln Trp Tyr Met His Leu Ser Lys Tyr Asn Val Lys Val
                325                 330                 335

Gly Asp Tyr Val Lys Ala Gly Gln Ile Ile Gly Trp Ser Gly Ser Thr
            340                 345                 350

Gly Tyr Ser Thr Ala Pro His Leu His Phe Gln Arg Met Val Asn Ser
        355                 360                 365

Phe Ser Asn Ser Thr Ala Gln Asp Pro Met Pro Phe Leu Lys Ser Ala
    370                 375                 380

Gly Tyr Gly Lys Ala Gly Gly Thr Val Thr Pro Thr Pro Asn Thr Gly
385                 390                 395                 400

Trp Lys Thr Asn Lys Tyr Gly Thr Leu Tyr Lys Ser Glu Ser Ala Ser
                405                 410                 415

Phe Thr Pro Asn Thr Asp Ile Ile Thr Arg Thr Thr Gly Pro Phe Arg
            420                 425                 430

Ser Met Pro Gln Ser Gly Val Leu Lys Ala Gly Gln Thr Ile His Tyr
        435                 440                 445

Asp Glu Val Met Lys Gln Asp Gly His Val Trp Val Gly Tyr Thr Gly
    450                 455                 460

Asn Ser Gly Gln Arg Ile Tyr Leu Pro Val Arg Thr Trp Asn Lys Ser
465                 470                 475                 480

Thr Asn Thr Leu Gly Val Leu Trp Gly Thr Ile Lys
                485                 490
```

<210> SEQ ID NO 7
<211> LENGTH: 741
<212> TYPE: DNA
<213> ORGANISM: Artificial Sequence
<220> FEATURE:
<223> OTHER INFORMATION: Description of Artificial Sequence: altered S. simulans lysostaphin gene

<400> SEQUENCE: 7

```
gctgcaacac atgaacattc agcacaatgg ttgaataatt acaaaaaagg atatggttac     60
ggtccttatc cattaggtat aaatggcggt atgcactacg gagttgattt ttttatgaat    120
attggaacac cagtaaaagc tatttcaagc ggaaaaatag ttgaagctgg ttggagtaat    180
tacggaggag gtaatcaaat aggtcttatt gaaaatgatg gagtgcatag acaatggtat    240
atgcatctaa gtaaatataa tgttaaagta ggagattatg tcaaagctgg tcaaataatc    300
ggttggtctg gaagcactgg ttattctaca gcaccacatt tacacttcca aagaatggtt    360
aattcatttt caaattcaac tgcccaagat ccaatgcctt tcttaaagag cgcaggatat    420
ggaaaagcag gtggtacagt aactccaacg ccgaatacag gttggaaaac aaacaaatat    480
ggcacactat ataaatcaga gtcagctagc ttcacaccta atacagatat aataacaaga    540
acgactggtc catttagaag catgccgcag tcaggagtct taaaagcagg tcaaacaatt    600
cattatgatg aagtgatgaa acaagacggt catgtttggg taggttatac aggtaacagt    660
ggccaacgta tttacttgcc tgtaagaaca tggaataaat ctactaatac tttaggtgtt    720
ctttggggaa ctataaagtg a                                              741
```

<210> SEQ ID NO 8
<211> LENGTH: 480
<212> TYPE: PRT
<213> ORGANISM: Staphylococcus simulans

<400> SEQUENCE: 8

```
Met Lys Lys Thr Lys Asn Asn Tyr Tyr Thr Pro Leu Ala Ile Gly
  1               5                  10                  15

Leu Ser Thr Phe Ala Leu Ala Ser Ile Val Tyr Gly Gly Ile Gln Asn
             20                  25                  30

Glu Thr His Ala Ser Glu Lys Ser Asn Met Asp Val Ser Lys Lys Val
         35                  40                  45

Ala Glu Val Glu Thr Ser Lys Pro Pro Val Glu Asn Thr Ala Glu Val
     50                  55                  60

Glu Thr Ser Lys Ala Pro Val Glu Asn Thr Ala Glu Val Glu Thr Ser
 65                  70                  75                  80

Lys Ala Pro Val Glu Asn Thr Ala Glu Val Glu Thr Ser Lys Ala Pro
                 85                  90                  95

Val Glu Asn Thr Ala Glu Val Glu Thr Ser Lys Ala Pro Val Glu Asn
            100                 105                 110

Thr Ala Glu Val Glu Thr Ser Lys Ala Pro Val Glu Asn Thr Ala Glu
        115                 120                 125

Val Glu Thr Ser Lys Ala Pro Val Glu Asn Thr Ala Glu Val Glu Thr
    130                 135                 140

Ser Lys Ala Pro Val Glu Asn Thr Ala Glu Val Glu Thr Ser Lys Ala
145                 150                 155                 160

Pro Val Glu Asn Thr Ala Glu Val Glu Thr Ser Lys Ala Pro Val Glu
                165                 170                 175

Asn Thr Ala Glu Val Glu Thr Ser Lys Ala Pro Val Glu Asn Thr Ala
            180                 185                 190

Glu Val Glu Thr Ser Lys Ala Pro Val Glu Asn Thr Ala Glu Val Glu
        195                 200                 205

Thr Ser Lys Ala Pro Val Glu Asn Thr Ala Glu Val Glu Thr Ser Lys
    210                 215                 220

Ala Leu Val Gln Asn Arg Thr Ala Leu Arg Ala Ala Thr His Glu His
225                 230                 235                 240

Ser Ala Gln Trp Leu Asn Asn Tyr Lys Tyr Gly Tyr Gly Tyr Gly Pro
                245                 250                 255

Tyr Pro Leu Gly Ile Asn Gly Gly Ile His Tyr Gly Val Asp Phe Phe
            260                 265                 270

Met Asn Ile Gly Thr Pro Val Lys Ala Ile Ser Ser Gly Lys Ile Val
        275                 280                 285

Glu Ala Gly Trp Ser Asn Tyr Gly Gly Asn Gln Ile Gly Leu Ile
    290                 295                 300

Glu Asn Asp Gly Val His Arg Gln Trp Tyr Met His Leu Ser Lys Tyr
305                 310                 315                 320

Asn Val Lys Val Gly Asp Tyr Val Lys Ala Gly Gln Ile Ile Gly Trp
                325                 330                 335

Ser Gly Ser Thr Gly Tyr Ser Thr Ala Pro His Leu His Phe Gln Arg
            340                 345                 350

Met Val Asn Ser Phe Ser Asn Ser Thr Ala Gln Asp Pro Met Pro Phe
        355                 360                 365

Leu Lys Ser Ala Gly Tyr Gly Lys Ala Gly Gly Thr Val Thr Pro Thr
```

|  | 370 |  |  |  | 375 |  |  |  | 380 |  |  |
|---|---|---|---|---|---|---|---|---|---|---|---|
| Pro | Asn | Thr | Gly | Trp | Lys | Thr | Asn | Lys | Tyr | Gly | Thr | Leu | Tyr | Lys | Ser |
| 385 | | | | | 390 | | | | | 395 | | | | | 400 |

Glu Ser Ala Ser Phe Thr Pro Asn Thr Asp Ile Ile Thr Arg Thr Thr
                    405                 410                 415

Gly Pro Phe Arg Ser Met Pro Gln Ser Gly Val Leu Lys Ala Gly Gln
                420                 425                 430

Thr Ile His Tyr Asp Glu Val Met Lys Gln Asp Gly His Val Trp Val
            435                 440                 445

Gly Tyr Thr Gly Asn Ser Gly Gln Arg Ile Tyr Leu Pro Val Arg Thr
        450                 455                 460

Trp Asn Lys Ser Thr Asn Thr Leu Gly Val Leu Trp Gly Thr Ile Lys
465                 470                 475                 480

<210> SEQ ID NO 9
<211> LENGTH: 1825
<212> TYPE: DNA
<213> ORGANISM: Staphylococcus simulans

<400> SEQUENCE: 9
gaaaattcca aaaaaaaacc tactttctta atattgattc atattatttt aacacaatca    60
gttagaattt caaaaatctt aaagtcaatt tttgagtgtg tttgtatatt tcatcaaagc   120
caatcaatat tattttactt tcttcatcgt taaaaaatgt aatatttata aaaatatgct   180
attctcataa atgtaataat aaattaggag gtattaaggt tgaagaaaac aaaaaacaat   240
tattatacga cacctttagc tattggactg agtacatttg ccttagcatc tattgtttat   300
ggagggattc aaaatgaaac acatgcttct gaaaaaagta aatgggatgt ttcaaaaaaa   360
gtagctgaag tagagacttc aaaaccccca gtagaaaata cagctgaagt agagacttca   420
aaagctccag tagaaaatac agctgaagta gagacttcaa aagctccagt agaaaataca   480
gctgaagtag agacttcaaa agctccagta gaaaatacag ctgaagtaga gacttcaaaa   540
gctccggtag aaaatacagc tgaagtagag acttcaaaag ctccggtaga aaatacagct   600
gaagtagaga cttcaaaagc cccagtagaa atacagctg aagtagagac ttcaaaagct   660
ccagtagaaa atacagctga gtagagact caaaagctc cggtagaaaa tacagctgaa   720
gtagagactt caaaagcccc agtagaaaat acagctgaag tagagacttc aaaagctcca   780
gtagaaaata cagctgaagt agagacttca aaagctccgg tagaaaatac agctgaagta   840
gagacttcaa agccccagt agaaaataca gctgaagtag agacttcaaa agccctggtt   900
caaaatagaa cagctttaag agctgcaaca catgaacatt cagcacaatg gttgaataat   960
tacaaaaaag gatatggtta cggtccttat ccattaggta taaatggcgg tatccactac  1020
ggagttgatt tttttatgaa tattggaaca ccagtaaaag ctatttcaag cggaaaaata  1080
gttgaagctg gttggagtaa ttcggagga ggtaatcaaa taggtcttat tgaaaatgat  1140
ggagtgcata gacaatggta tatgcatcta agtaaatata atgttaaagt aggagattat  1200
gtcaaagctg tcaaataat cggttggtct ggaagcactg ttattctac agcaccacat  1260
ttacacttcc aaagaatggt taattcattt tcaaattcaa ctgcccaaga tccaatgcct  1320
ttcttaaaga gcgcaggata tggaaaagca ggtggtacga taactccaac gcccaataca  1380
ggttggaaaa caaacaaata tggcacacta tataatcag agtcagctag cttcacacct  1440
aatacagata taataacaag aacgactggt ccatttagaa gcatgccgca gtcaggagtc  1500
ttaaaagcag gtcaaacaat tcattatgat gaagtgatga acaagacgg tcatgtttgg  1560

-continued

| | |
|---|---|
| gtaggttata caggtaacag tggccaacgt atttacttgc ctgtaagaac atggaataaa | 1620 |
| tctactaata ctttaggtgt tctttgggga actataaagt gagcgcgctt tttataaact | 1680 |
| tatatgataa ttagagcaaa taaaaatttt ttctcattcc taaagttgaa gcttttcgta | 1740 |
| atcatgtcat agcgtttcct gtgtgaaatt gcttagcctc acaattccac acaacatacg | 1800 |
| agccggaaca taaagtgcta agcct | 1825 |

<210> SEQ ID NO 10
<211> LENGTH: 6457
<212> TYPE: DNA
<213> ORGANISM: Achromobacter lyticus

<400> SEQUENCE: 10

| | |
|---|---|
| gatatcattt caaagacaga tattctaaag aaaagatata ttttaaaaaa tgtggttgaa | 60 |
| aaaattaaag aaattcacga ttttgactat atatttattg atgtaccacc tactattaac | 120 |
| tctgatttca ctaataatgc tgtttacgca agtgattaca ttttaatggt atttcaaaca | 180 |
| caacaatctg cttatgaaag tagtctttca tttgttaatt ttttaaggga tcgaaaaaaa | 240 |
| gaatcagatt tatcatttga attggttggc gctgttccag tattaattaa aaaaagtgga | 300 |
| cgtgtagata acagatatt agatatgtct aaatcagcat tttctgaagc actctttgag | 360 |
| aaccagatat atcaaagaga aagaataaaa aaatttgccg ctgatggaat aaaagataaa | 420 |
| gatatgcatg acaaaaaagt tatatatatg tttaacaaag tctacgaaga attagttgat | 480 |
| agagttagat taattgaagg tgagtgatat ttatggcagg attttttagat aacatagata | 540 |
| catctgaggt aaaatatacg gaaaattata accggtatc taaagtacg actatgagag | 600 |
| tggacactga tataaaaaaa agattaaatc aaatggcgtt agataaagat acatctataa | 660 |
| aggctatagt tgatgaagtg ttaggagaat ttttgaaaaa aataagtat tagtatttta | 720 |
| tataggctct atactattta ggactggtga taatcactag tcctattttt gatacaaaaa | 780 |
| agcgcaatta tctctataat tagaagtatc ctaccaccaa taattaagga ataatgcgc | 840 |
| ctatgtctaa tattatatca atcaccctg gaattaaaga taaaaatatc acttttgaag | 900 |
| ataaggttga agaaagtata aagggaaaaa ttctttatt tactttggaa aattaataca | 960 |
| ttctcccaag cgatgtaaac tttgcggaca cgaaaatacg aacttttcta taatcaaaaa | 1020 |
| tggttttaaa aaatcatgtc ttacgatacc taaggtatcg gagaagccag cttatttaat | 1080 |
| attggaaaaa cagcgtttcc actgtaaaaa gtgctgcagt tatttcactg ctgaaacacc | 1140 |
| tgtcgttgag tggaattgct atatttctca aaacacacga ttagctgtgc tgaataagtc | 1200 |
| gatagacata cgttcgcaaa atctgttgc tgaatcttgt catgtcagta attccacagt | 1260 |
| tactcgaata attaataaag ctgcttctca aatagctcaa acaccgttta atatttacc | 1320 |
| ggaacacttg atgatggatg agttcaaaag cgttaaaaat gttgtcggta aaatgagttt | 1380 |
| tatttatgca gatgcagtaa cacaccgtat tattgatatt gtgcctgacc gcaggttatt | 1440 |
| tgctttgaaa aattatttct accgttatcc tctttctgaa agaaaatgtg tgaaagcagt | 1500 |
| gtctattgat atgtatgaac cttatatggc tttgatcaga gaagtttttc ctaatgccaa | 1560 |
| aattctaata gttcatttcc atattgttca gtctttaaat aaagccttga acatgactcg | 1620 |
| agtaacagtt atgaatagtt tcagaacaac tgaaagacct ctatacaaca agtacaagcg | 1680 |
| ttactggaag attcttttaa aactgccttg aaaaatatag aaatcaatag cgttgctcct | 1740 |
| aaacttcaaa cagctgttaa aacactaaga aagcacaata gaatgataag aaatacttt | 1800 |

```
gaatacagta acttgaccaa cggttcactt gagggaataa atactaaaat aaagctgata    1860
cagagaatat cttttggtta tagaaatttt ggtgatttac gcagtcgtat cattttatgt    1920
acaaatcttt ttgcagctaa tccaaaaaaa gagatcaagc aactttatgc tgcttaatct    1980
ctgcgtttta gctcaccagt cttatttgac agagagccaa taaaattaac ggagggagaa    2040
ggattcgaac caacgcaagc acatacatgc tcctaattaa taaaaatata ttaatcccct    2100
taatccagac ttgggtatcc ctccacaagc attatttaat gctaatataa catatataac    2160
aacaaatgtc aatatgtatt tataaggaaa aggatattaa aattattctg agttatataa    2220
ggtagtattc ataatcatcc taaagttgaa gtcgaaaagc ttcaactttta ggaatgagaa    2280
aaaattttta tttgctctaa ttatcatata agtttataaa aagcgcgctc actttatagt    2340
tccccaaaga acacctaaag tattagtaga tttattccat gttcttacag gcaagtaaat    2400
acgttggcca ctgttacctg tataacctac ccaaacatga ccgtcttgtt tcatcacttc    2460
atcataatga attgttgac ctgcttttaa gactcctgac tgcggcatgc ttctaaatgg    2520
tagtgtgcca cttgttatta tatctgtatt aggtgtgaag ctagctgact ctgatttata    2580
accagtcgtt tatttgtttg ttttccaacc tgtattcggc gttggagtta ctgtaccacc    2640
tgcttttcca tatcctgcgc tctttaagaa aggcattgga tcttgggcag ttgaatttga    2700
aaatgaatta accattcttt ggaagtgtaa atgtggtgct gtagaataac cagtgcttcc    2760
agaccaaccg attatttgac cagctttgac ataatctcct actttaacat tatatttact    2820
tagatgcata taccattgtc tatgcactcc atcattttca ataagaccta tttgattacc    2880
tcctccgtaa ttactccaac cagcttcaac tattttttccg cttgaaatag cttttactgg    2940
tgttccaata ttcataaaaa aatcaactcc gtagtgcata ccgccattta tacctaatgg    3000
ataaggaccg taaccatatc cttttttgta attattcaac cattgtgctg aatgttcatg    3060
tgttgcagct cttaaagctg ttctattttg aaccagggct tttgaagtct ctacttcagc    3120
tgtatttct actggggctt ttgaagtctc tacttcagct gtattttcta ccggagcttt    3180
tgaagtctct acttcagctg tattttctac tggagcttt gaagtctcta cttcagctgt    3240
attttctact ggggcttttg aagtctctac ttcagctgta ttttctaccg gagcttttga    3300
agtctctact tcagctgtat tttctactgg agcttttgaa gtctctactt cagctgtatt    3360
ttctactggg gcttttgaag tctctacttc agctgtattt tctaccggag cttttgaagt    3420
taccggagct tttgaagtct ctacttcagt gtattttcta ctggagcttt tgaagtctct    3480
acttcagctg tattttctac tggagctttt gaagtctcta cttcagctgt attttctact    3540
ggagcttttg aagtctctac ttcagctgta ttttctactg ggcttttga agtctctact    3600
tcagctactt tttttgaaac atccatatta ctttttttcag aagcatgtgt ttcattttga    3660
atccctccat aaacaataga tgctaaggca aatgtactca gtccaatagc taaaggtctc    3720
gtataataat tgttttttgt tttcttcaac cttaatacct cctaatttat tattcatttt    3780
atgagaatag catattttta taaatattac atttttttaac gatgaagaaa gtaaaataat    3840
attgattgat tttgatgaaa tatacaaaca cactcaaaaa ttgactttaa gattttttgaa    3900
attctaactg attgtgttaa aataatatga atcaatatta agaaagtagg ttttttttttg    3960
gaattttcaa aactaaacat tcaagagttc gaagaatttg tgtttcaaaa aatgtctcat    4020
tacacacaat ctgcttctca ttttgaatat agaaataacc atcagaataa tgtgcattta    4080
gttggcgtaa aaaatgaaac aggtgaagta ttagctgctt gttactgac tgaggcacgt    4140
tgtttaaagt tcttaaata tttctataca catcgcggtc cagtcatgaa ctttaaagac    4200
```

-continued

```
catgagttag tcagattttt ttatgaaaac ttaacgacct atctaaaaaa gcaaaactgc    4260
ttatatgttt taactgaccc ttacctgtta gaaaatattc gaagttgtga cggagaaatc    4320
cttgaatctt atgataacga aacttttatg aacgtgatga atttattagg ttaccgtcat    4380
caagggttta ctacaggtta ttctcaaaca agtcagatca gatggttgtc ggtcttaaac    4440
ctagaaaata aagatgaaaa acaattgtta aagaaatgg attatcaaac acgccgtaat    4500
attaagaaaa cctatgaaat gcaggtgaaa gtccgcgatt tatcaattaa tgaaacagat    4560 cgattttta aattatttaa aatggctgaa gaaaaacatg gcttcaaata agttattttg    4620
aaagaatgca gaaaacatac gctgataata gtatgttaaa gctggcttac atcgatttag    4680
aagaattatt agagacacaa aatgcgaaag tcgctgagtt aaatacagat attgaaaata    4740
ttcaagcggc attaaaagaa aaccctaatt ctaagaaaaa caaaaataaa tatgcgcaat    4800
accaaaagca attagcagca caagaacgaa aaattactga acgaaaaaa ttgatagaaa    4860 cagatggacc tgtattagac ttagctgcag cttactatat ctataccct catgaagttt    4920 actacctatc cagtggttca aaccctaaat acaatgccta tgggtgcg tacagactcc    4980 aatgggaaat gattcaattt gcgaaaaata aggtattaa tcgctataat ttttacggta    5040
ttacaggaga tttcagtgaa gatgctgaag atttcggtgt tcaaaaattc aaagaaggct    5100
ttaatgccca tgttgaagaa tatgtcggcg acttcattaa accgattaaa cctttatttt    5160
ataaaattca tcaattatta aatagataac tgaaaattat ttagtctttg ttaatcaaat    5220
atgacacctc aaaatgggtg tgaagagaac tatattttca aaggcgttaa tctcgacatc    5280
agcgaaggta aacgttctag ttttacattc ttaactacta agatgctata atttggttaa    5340
cgaagattat atgcatatta agcacctact tccatcgaaa atatcgccgg aagataagac    5400
gactatatta ttataccatc tgtaaatata caagcatata tacttctgat aacagaacct    5460
tgtagctgat gctggctatg gtagtaaaag taaggttttg tttcaaagta aaaaatatag    5520
ctaaccacta atttatcatg tcagtgttca ctcaacttgc tagcatgatg ctaatttcgt    5580
ggcatggcga aaatccgtag atctgaagag atctgcggtt cttttatat agaccgtaaa    5640 tacattcaat accttttaaa gtattctttg ccgtattgat actttgatac cttgtctttc    5700
ttactttaat atgacggtgg ccttgctcaa taaggttatt ccgatatttc gatgtacaat    5760
gacagtcatg tttaagttta aaagctttaa tgactttagc catggctacc ttcgttgaag    5820
gtgcctgatc tgtaattacc ttttgaggtt taccaaattg tttaatgaga cgtttgataa    5880
acgcatatgc tgaatgatta tctcgttgct tacgcaagca aatatctaat gtatgggttc    5940
tgtaaaaatt aatactttag aaaacccagc attatatgta tcactgatat ttatattttat    6000 atttcatata aatacttgaa caaaaaattc atatttaatt ttctttgttg actaacaata    6060
tttatttata agtatttgct gtcattattc taatttatgg aggccgtttt ttatgaactt    6120
taaatatttg tatgagaaat tttcttggat gagtcttgct tggatttttag tgtcatgcag    6180 tgtcttaagt ggtattctga ctcccttttg ggaattccaa taggtattat tttaggctta    6240
tatttggatg gattactaaa aaaggatgct tcttgatatt aacttaattt ttaataactc    6300
cagctaatta ctgttaaagt tgtataatta ttaaattaag gaaacattac aagaaaagga    6360
aatgcatatt tgtatttcct tttcttgtaa tgttataaaa attaagatgt tataccctat    6420
ctttattaat gctataaacc gtctgccttg tgatatc                             6457
```